(12) United States Patent
Teufel et al.

(10) Patent No.: US 10,532,106 B2
(45) Date of Patent: Jan. 14, 2020

(54) BICYCLIC PEPTIDE LIGANDS SPECIFIC FOR MT1-MMP

(71) Applicant: BicycleRD Limited, Cambridgeshire (GB)

(72) Inventors: Daniel Paul Teufel, Cambridge (GB); Catherine Lucy Stace, Cambridge (GB); Silvia Pavan, Cambridge (GB); Edward Walker, Cambridge (GB); Leonardo Baldassare, Cambridge (GB)

(73) Assignee: BICYCLERD LIMITED, Cambridge (GB)

(*) Notice: Subject to any disclaimer, the term of this patent is extended or adjusted under 35 U.S.C. 154(b) by 45 days.

(21) Appl. No.: 15/523,266

(22) PCT Filed: Oct. 29, 2015

(86) PCT No.: PCT/GB2015/053247
§ 371 (c)(1),
(2) Date: Apr. 28, 2017

(87) PCT Pub. No.: WO2016/067035
PCT Pub. Date: May 6, 2016

(65) Prior Publication Data
US 2018/0280525 A1    Oct. 4, 2018

(30) Foreign Application Priority Data

Oct. 29, 2014  (GB) .................................. 1419237.1
Aug. 27, 2015  (GB) .................................. 1515245.7

(51) Int. Cl.
| | | |
|---|---|---|
| C07K 7/08 | (2006.01) |
| A61K 47/64 | (2017.01) |
| A61K 51/04 | (2006.01) |
| A61K 51/08 | (2006.01) |
| A61K 47/54 | (2017.01) |
| A61K 31/195 | (2006.01) |
| C07K 7/02 | (2006.01) |
| A61P 35/00 | (2006.01) |

(52) U.S. Cl.
CPC ............ *A61K 47/64* (2017.08); *A61K 31/195* (2013.01); *A61K 47/547* (2017.08); *A61K 51/0482* (2013.01); *A61K 51/08* (2013.01); *C07K 7/02* (2013.01); *C07K 7/08* (2013.01); *A61P 35/00* (2018.01)

(58) Field of Classification Search
None
See application file for complete search history.

(56) References Cited

U.S. PATENT DOCUMENTS

| | | |
|---|---|---|
| 2012/0172235 A1 | 7/2012 | Winter et al. |
| 2014/0163201 A1 | 6/2014 | Winter et al. |
| 2014/0274759 A1 | 9/2014 | Walker et al. |
| 2018/0169254 A1 | 6/2018 | Bennett et al. |

FOREIGN PATENT DOCUMENTS

| | | |
|---|---|---|
| CN | 101497878 | 8/2009 |
| FR | 2932189 | 12/2009 |
| WO | WO 2009/098450 | 8/2009 |
| WO | WO 2010/089117 | 8/2010 |
| WO | WO 2013/050615 | 4/2013 |
| WO | WO 2016/067035 | 5/2016 |

OTHER PUBLICATIONS

National Institute of Cancer—understanding and related topics, accessed Aug. 21, 2014 at URL: cancer.gov/cancertopics/understandingcancer, 63 pages.*
Merck Manuals Lung Carcinoma accessed Mar. 12, 2017 at URL merckmanuals.com/professional/pulmonary-disorders/tumors-of-the-lungs/lung-carcinoma, 18 pages.*
Merck Manuals Neuroblastoma accessed Mar. 12, 2017 at URL merckmanuals.com/professional/ pediatrics/pediatric-cancers/neuroblastoma, 4 pages.*
Cholangiocarcinoma accessed Mar. 12, 2017 at URL surgery.usc.edu/divisions/turnor/pancreasdiseases/web%20pages/BILIARY%20SYSTEM/cholangiocarcinorna, 2 pages.*
Thyroid cancer accessed Mar. 12, 2017 at URL www.merckmanuals.com/professional/endocrine-and-metabolic-disorders/thyroid-disorders/thyroid-cancers, 4 pages.*
Merck Manual Colorectal Cancer accessed Aug. 21, 2014 at URL merckmanuals.com/home/digestive_disorders/tumors_of_the_digestive_system/colorectal_cancer.htm, 5 pages.*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages.*
Renal cell carcinoma, accessed Mar. 12, 2017 at URL merckmanuals.com/professional/genitourinary-disorders/genitourinary-cancer/renal-cell-carcinoma, 6 pages.*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages.*
Remacle et al., "Membrane type I-matrix metalloproteinase (MT1-MMP) is internalized by two different pathways and is recycled to the cell surface," J. Cell Sci. 116: 3905-3916 (2003).*

(Continued)

*Primary Examiner* — Julie Ha
*Assistant Examiner* — Kristina M Hellman
(74) *Attorney, Agent, or Firm* — Andrea L. C. Reid; Dechert LLP

(57) ABSTRACT

The present invention relates to polypeptides which are covalently bound to molecular scaffolds such that two or more peptide loops are subtended between attachment points to the scaffold. In particular, the invention describes peptides which are high affinity binders of membrane type 1 metalloprotease (MT1-MMP). The invention also describes drug conjugates comprising said peptides, conjugated to one or more effector and/or functional groups which have utility in imaging and targeted cancer therapy.

12 Claims, 11 Drawing Sheets

Specification includes a Sequence Listing.

(56) References Cited

OTHER PUBLICATIONS

Zarrabi et al., "Inhibition of Matrix Metalloproteinase 14 (MMP-14)-mediated Cancer Cell Migration," J. Biol. Chem. 286: 33167-33177 (2011).*
Angelini et al., "Bicyclic peptide inhibitor reveals large contact interface with a protease target", ACS Chemical Biology, vol. 7, No. 5, pp. 817-821 (2012).
Heinis et al., "Phage-encoded combinatorial chemical libraries based on bicyclic peptides", Nature Chemical Biology, vol. 5, No. 7, pp. 502-507 (2009).
International Search Report from PCT Patent Application No. PCT/GB2015/053247 dated Jan. 27, 2016, application now published as International Publication No. WO 2016/067035 dated May 6, 2016.
Remacle et al., "Novel MT1-MMP small-molecule inhibitors based on insights into hemopexin domain function in tumor growth", Cancer Res., vol. 72, No. 9, pp. 2339-2349 (2012).
Suojanen et al., "A novel and selective membrane type-1 matrix metalloproteinase (MT1-MMP) inhibitor reduces cancer cell motility and tumor growth", Cancer Biol. Ther., vol. 8, No. 24, pp. 2362-2370 (2009).
Thevenard et al., "The YSNSG cyclopeptide derived from tumstatin inhibits tumor angiogenesis by down-regulating endothelial cell migration", Int. J. Cancer, vol. 126, No. 5, pp. 1055-1066 (2010).
Zarrabi et al., "Inhibition of matrix metalloproteinase 14 (MMP-14)-mediated cancer cell migration", J. Biol. Chem., vol. 286, No. 38, pp. 33167-33177 (2011).

* cited by examiner

A

B

BICYCLIC PEPTIDE LIGANDS SPECIFIC FOR MT1-MMP

CROSS-REFERENCE TO RELATED APPLICATIONS

This application is a U.S. National Stage of International Patent Application No. PCT/GB2015/053247, filed Oct. 29, 2015, which claims the benefit of priority of GB Application No. 1419237.1, filed Oct. 29, 2014, and GB Application No. 1515245.7, filed Aug. 27, 2015, all of which are incorporated herein by reference in their entirety.

A Sequence Listing is being submitted electronically via EFS in the form of a text file created Nov. 1, 2019 and named "392664-022US_163628_SL_20191101.txt" (23,877 bytes), the contents of which are incorporated herein by reference in their entirety.

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of membrane type 1 metalloprotease (MT1-MMP). The invention also describes drug conjugates comprising said peptides, conjugated to one or more effector and/or functional groups which have utility in imaging and targeted cancer therapy.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a peptide ligand specific for MT1-MMP comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises an amino acid sequence of formula (I):

(I)
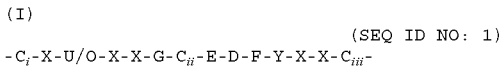
$-C_i-X-U/O-X-X-G-C_{ii}-E-D-F-Y-X-X-C_{iii}-$ or a modified derivative, or pharmaceutically acceptable salt, thereof;

wherein:

$C_i$, $C_{ii}$, and $C_{iii}$ represent first, second and third cysteine residues, respectively;

X represents any amino acid residue;

U represents a polar, uncharged amino acid residue selected from N, C, Q, M, S and T; and O represents a non-polar aliphatic amino acid residue selected from G, A, I, L, P and V.

According to a further aspect of the invention, there is provided a drug conjugate comprising a peptide ligand as defined herein conjugated to one or more effector and/or functional groups, such as a cytotoxic agent, in particular DM1 and MMAE.

According to a further aspect of the invention, there is provided a conjugate comprising a peptide ligand as defined herein conjugated to one or more effector and/or functional groups, such as a radionuclide bearing chelator group, in particular DOTA.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand as defined herein for use in preventing, suppressing or treating cancer, in particular solid tumours such as non-small cell lung carcinomas.

DETAILED DESCRIPTION OF THE INVENTION

Figure 1:
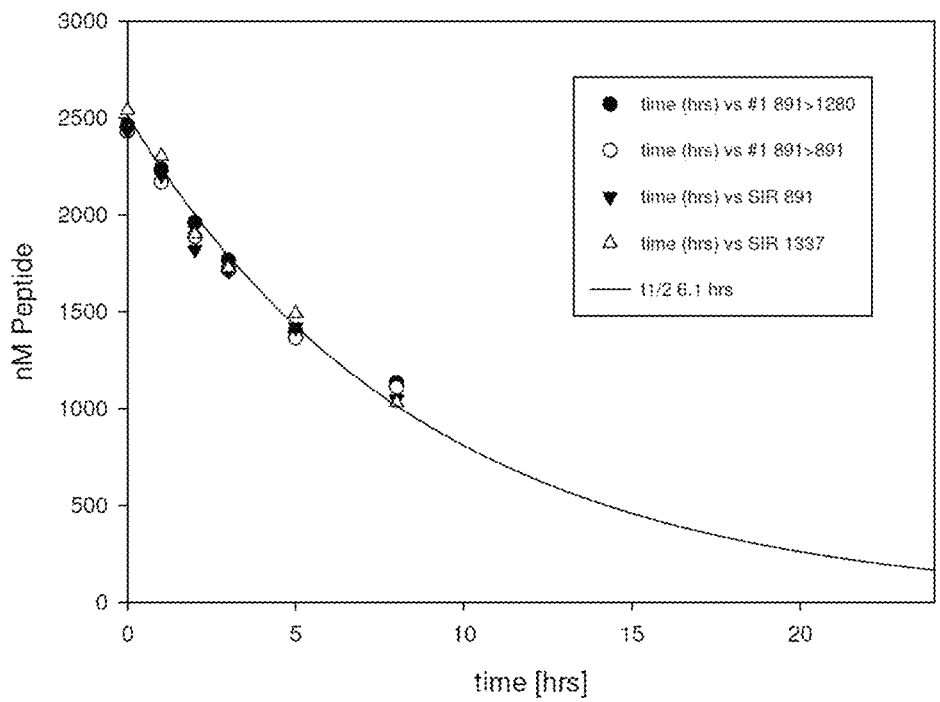
FIG. 1: Mouse Plasma Stability of 17-69-07-N219. Several ions were monitored as indicated in the legend, as well as two transitions in MRM mode. There is an excellent correlation between the ions. The half-life of the peptide in mouse plasma at 37° C. is 6 hours.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Nomenclature

Numbering

When referring to amino acid residue positions within compounds of formula (I), cysteine residues ($C_i$, $C_{ii}$ and $C_{iii}$) are omitted from the numbering as they are invariant, therefore, the numbering of amino acid residues within the compound of formula (I) is referred to as below:

(SEQ ID NO: 1)
-$C_i$-$X_1$-U/$O_2$-$X_3$-$X_4$-$G_5$-$C_{ii}$-$E_6$-$D_7$-$F_8$-$Y_9$-$X_{10}$-$X_{11}$-

$C_{iii}$-.

For the purpose of this description, all bicyclic peptides are assumed to be cyclised with TBMB (1,3,5-tris(bromomethyl)benzene) yielding a tri-substituted 1,3,5-trismethyl-benzene structure. Cyclisation with TBMB occurs on $C_i$, $C_{ii}$, and $C_{iii}$.

Bicyclic Peptide Core Sequence

Each bicyclic peptide disclosed herein has been assigned a unique core sequence number which is defined as the amino acid sequence between the first N-terminal Cysteine ($C_i$) and the last C-terminal Cysteine ($C_{iii}$). In the example of the identifier 17-69-07, the core sequence is $C_i$YNEF-G$C_{ii}$EDFYDI$C_{iii}$ (SEQ ID NO: 2), and is referred to as "17-69-07" or "(17-69-07)".

Peptide Code

Certain bicyclic peptides disclosed herein have also been assigned a unique identifier using a peptide code, such as 17-69-07-N241, wherein N241 denotes a particular derivative of the 17-69-07 bicycle core sequence. Different derivatives of 17-69-07 have different N-numbers, i.e. N001, N002, Nxxx.

Molecular Format

N- or C-terminal extensions to the bicycle core sequence are added to the left or right side of the core sequence, separated by a hyphen. For example, an N-terminal βAla-Sar10-Ala tail would be denoted as:

βAla-Sar10-A-(17-69-07)

and has the full sequence of βAla-Sar10-A-CYNEF-GCEDFYDIC (SEQ ID NO: 3).

Modifications

Non-natural amino acid substitutions within the bicycle core sequence are indicated after the Molecular Format description. For example, if Tyrosine 1 in 17-69-07 is substituted with D-Alanine, the description is (17-69-07) D-Ala1, and the full sequence would be described as C(D-Ala1)NEFGCEDFYDIC (SEQ ID NO: 4).

If an N-terminal or C-terminal tail is attached to a bicyclic peptide that also contains modifications to the core sequence, then, by using 17-69-07-N241 as an example, the Molecular Format description is:

βAla-Sar10-A-(17-69-07) DAla1 1NAl4 DAla5 tBuGly11.

The full amino acid sequence of 17-69-07-N241 is therefore:

(SEQ ID NO: 5)
βAla-Sar10-A-C(D-Ala)NE(1Nal)(D-

Ala)CEDFYD(tBuGly)C.

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Figure 8:
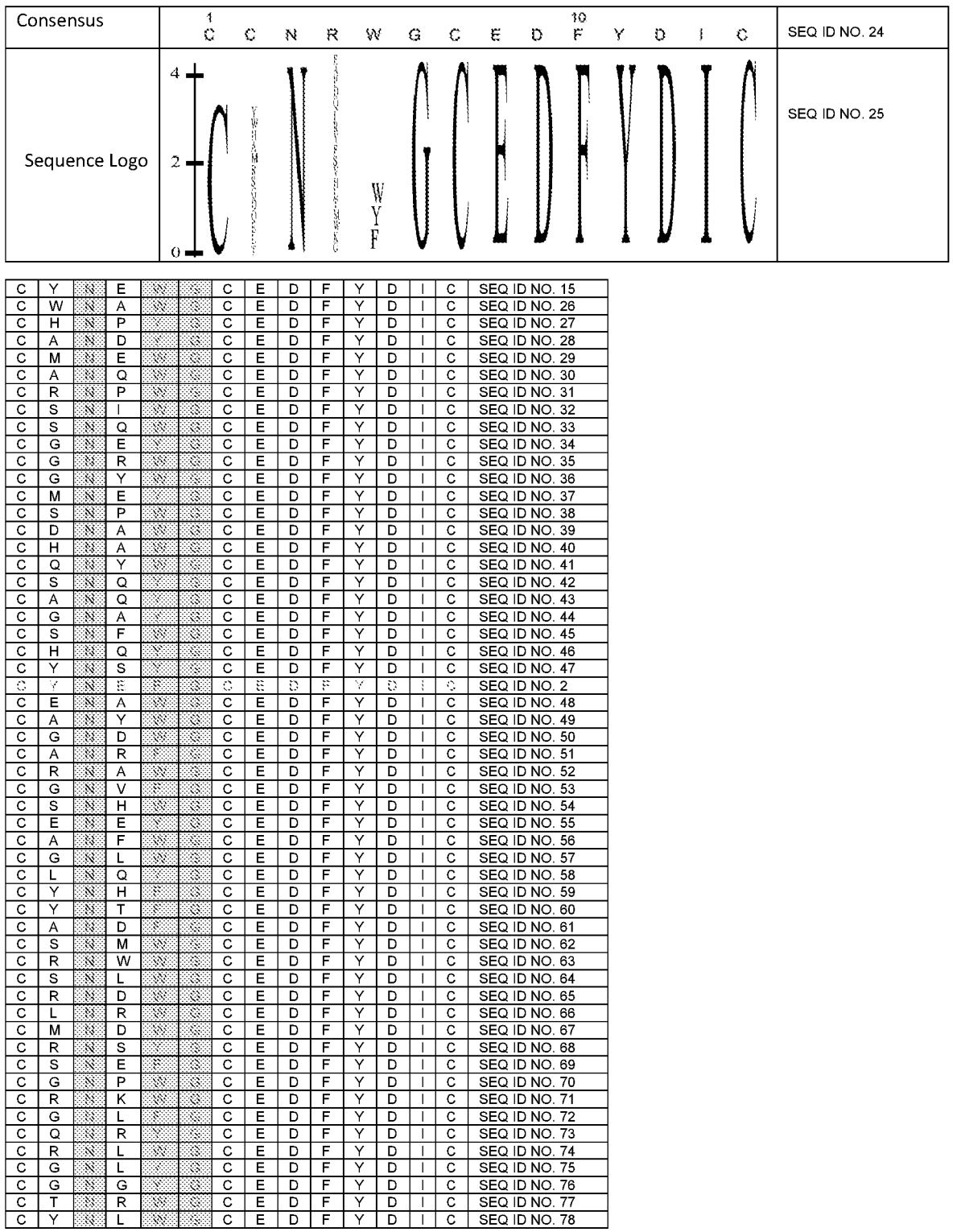
FIG. 8: List of sequence outputs derived from affinity maturations using libraries with fixed loop 2 residues of 17-69. The sequence logo plot on the right shows the overall preference of the residues in loop1 residues 1, 2, 3, 4 and 5.

It will be appreciated by the skilled person that the X at positions 1, 3, 4, 10 and 11 of formula (I) may represent any amino acid following the results of the alanine scan (see Table 5) and selection outputs (FIG. 8) which permits well tolerated substitutions at these positions.

In one embodiment, the X at position 1 of formula (I) is selected from any one of the following amino acids: Y, M, F or V. In a further embodiment, the X at position 1 of formula (I) is selected from Y, M or F. In a yet further embodiment, the X at position 1 of formula (I) is selected from Y or M. In a still yet further embodiment, the X at position 1 of formula (I) is selected from Y.

In one embodiment, the U/O at position 2 of formula (I) is selected from a U, such as an N. In an alternative embodiment, the U/O at position 2 of formula (I) is selected from an O, such as a G.

In one embodiment, the X at position 3 of formula (I) is selected from U or Z, wherein U represents a polar, uncharged amino acid residue selected from N, C, Q, M, S and T and Z represents a polar, negatively charged amino acid residue selected from D or E. In a further embodiment, the U at position 3 of formula (I) is selected from Q. In an alternative embodiment, the Z at position 3 of formula (I) is selected from E.

In one embodiment, the X at position 4 of formula (I) is selected from J, wherein J represents a non-polar aromatic amino acid residue selected from F, W and Y. In a further embodiment, the J at position 4 of formula (I) is selected from F. In alternative embodiment, the J at position 4 of formula (I) is selected from Y. In alternative embodiment, the J at position 4 of formula (I) is selected from W.

In one embodiment, the X at position 10 of formula (I) is selected from Z, wherein Z represents a polar, negatively charged amino acid residue selected from D or E. In one embodiment, the Z at position 10 of formula (I) is selected from D.

In one embodiment, the X at position 11 of formula (I) is selected from O, wherein O represents a non-polar aliphatic amino acid residue selected from G, A, I, L, P and V. In one embodiment, the O at position 11 of formula (I) is selected from I.

In one embodiment, the compound of formula (I) is a compound of formula (Ia):

(Ia)
(SEQ ID NO: 6)
$C_i$-Y/M/F/V-U/O/Z-J-G-$C_{ii}$-E-D-F-Y-Z-O-$C_{iii}$-;

wherein U, O, J and Z are as defined hereinbefore.

In one embodiment, the compound of formula (I) is a compound of formula (Ib):

(Ib)
(SEQ ID NO: 7)
-$C_i$-Y/M/F/V-N/G-E/Q-F-G-$C_{ii}$-E-D-F-Y-D-I-$C_{iii}$-.

In one embodiment, the compound of formula (I) is a compound of formula (Ic):

(Ic)
(SEQ ID NO: 8)
-$C_i$-Y/M/F-N/G-E/Q-F-G-$C_{ii}$-E-D-F-Y-D-I-$C_{iii}$-.

In one embodiment, the compound of formula (I) is a compound of formula (Id):

(Id)
(SEQ ID NO: 9)
-$C_i$-Y/M-N-E/Q-F-G-$C_{ii}$-E-D-F-Y-D-I-$C_{iii}$-.

In one embodiment, the compound of formula (I) is a compound of formula (Ie):

(Ie)
(17-69-07)
(SEQ ID NO: 2)
-$C_i$-Y-N-E-F-G-$C_{ii}$-E-D-F-Y-D-I-$C_{iii}$-.

In a yet further embodiment, the peptide of formula (I) comprises a sequence selected from:

(17-69-07)
(SEQ ID NO: 2)
-$C_i$-Y-N-E-F-G-$C_{ii}$-E-D-F-Y-D-I-$C_{iii}$-;

(17-69-12)
(SEQ ID NO: 10)
-$C_i$-M-N-Q-F-G-$C_{ii}$-E-D-F-Y-D-I-$C_{iii}$-;

(17-69-02)
(SEQ ID NO: 11)
-$C_i$-F-G-E-F-G-$C_{ii}$-E-D-F-Y-D-I-$C_{iii}$-;

(17-69-03)
(SEQ ID NO: 12)
-$C_i$-V-N-E-F-G-$C_{ii}$-E-D-F-Y-D-I-$C_{iii}$-;

(17-69-04)
(SEQ ID NO: 13)
-$C_i$-F-N-E-F-G-$C_{ii}$-E-D-F-Y-D-I-$C_{iii}$-;

(17-69-07-N057)
(SEQ ID NO: 14)
-$C_i$-Y-N-E-Y-G-$C_{ii}$-E-D-F-Y-D-I-$C_{iii}$-;
and (17-69-44-N002)
(SEQ ID NO: 15)
-$C_i$-Y-N-E-W-G-$C_{ii}$-E-D-F-Y-D-I-$C_{iii}$-.

The peptides of this embodiment were identified to be potent candidates following affinity maturation against the hemopexin domain of MT1-MMP (see Example 1 and Tables 1 and 8).

In a still yet further embodiment, the peptide of formula (I) comprises a sequence selected from:

(17-69-07)
(SEQ ID NO: 2)
-$C_i$-Y-N-E-F-G-$C_{ii}$-E-D-F-Y-D-I-$C_{iii}$-;
and (17-69-12)
(SEQ ID NO: 10)
-$C_i$-M-N-Q-F-G-$C_{ii}$-E-D-F-Y-D-I-$C_{iii}$-.

The peptides of this embodiment were identified to be the highest affinity candidates following affinity maturation against the hemopexin domain of MT1-MMP, synthesis of the core bicycle sequences, and quantitative measurement of affinities using competition experiments (see Example 1 and Tables 1-3).

In a still yet further embodiment, the peptide of formula (I) comprises a sequence selected from -$C_i$-Y-N-E-F-G-$C_{ii}$-E-D-F-Y-D-I-$C_{iii}$- (17-69-07) (SEQ ID NO: 2). The peptide of this embodiment was identified to be the most potent, and stable member of the family of peptide ligands within formula (I) (see Examples 1 to 4).

In one embodiment, certain peptide ligands of the invention are fully cross-reactive with murine, dog, cynomolgus and human MT1-MMP. In a further embodiment, the specifically exemplified peptide ligands of the invention are fully cross-reactive with murine, dog, cynomolgus and human MT1-MMP. For example, data is presented herein which demonstrates that both non-stabilised and stabilised derivatives of 17-69-07 (i.e. 17-69-07-N219 and 17-69-07-N241) are fully cross reactive (see Table 13).

In a yet further embodiment, the peptide ligand of the invention is selective for MT1-MMP, but does not cross-react with MMP-1, MMP-2, MMP-15 and MMP-16. Data is presented herein which demonstrates that the 17-69-07 core sequence, and the stabilised variant 17-69-07-N258, are uniquely selective for MT1-MMP (see Table 14).

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Pharmaceutically Acceptable Salts

It will be appreciated that salt forms are within the scope of this invention, and references to compounds of formula (I) include the salt forms of said compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^+$ and Mg$^+$, and other cations such as Al$^+$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of formula (I) contain an amine function, these may form quaternary ammonium salts, for example by reaction with an alkylating agent according to methods well known to the skilled person. Such quaternary ammonium compounds are within the scope of formula (I).

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyn-group bearing amino acids that allow functionalisation with alkyn or azide-bearing moieties, respectively.

In one embodiment, the modified derivative comprises a modification at amino acid position 1 and/or 9. Data is presented herein which shows that these positions, especially where tyrosine is present, are most susceptible to proteolytic degradation.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group, such as 17-69-07-N004 disclosed herein. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target, such as an Ala, G-Sar10-A or bAla-Sar10-A group. Data is presented herein which shows that addition of these groups to the bicyclic peptide 17-69-07 does not alter potency to the target protein (Tables 11-12).

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the non-natural amino acid residue is substituted at position 4. Data is presented herein which shows that a number of non-natural amino acid residues are well tolerated at this position (see Table 8). In a further embodiment, the non-natural amino acid residues, such as those present at position 4, are selected from: 1-naphthylalanine; 2-naphthylalanine; cyclohexylglycine, phenylglycine; tert-butylglycine; 3,4-dichlorophenylalanine; cyclohexylalanine; and homophenylalanine.

In a yet further embodiment, the non-natural amino acid residues, such as those present at position 4, are selected from: 1-naphthylalanine; 2-naphthylalanine; and 3,4-dichlorophenylalanine. Data is presented herein which shows that these substitutions enhanced the affinity compared to the unmodified wildtype sequence (see Table 8).

In a yet further embodiment, the non-natural amino acid residues, such as those present at position 4, are selected from: 1-naphthylalanine. Data is presented herein which shows that this substitution provided the greatest level of enhancement of affinity (greater than 7 fold) compared to wildtype (see Table 8).

In one embodiment, the non-natural amino acid residue is introduced at position 9 and/or 11. Data is presented herein which shows that a number of non-natural amino acid residues are well tolerated at these positions (see Table 9).

In a further embodiment, the non-natural amino acid residues, such as those present at positions 9, are selected from: 4-bromophenylalanine, pentafluoro-phenylalanine.

In a further embodiment, the non-natural amino acid residues, such as those present at positions 11, are selected from: tert-butylglycine.

In a yet further embodiment, the non-natural amino acid residues, such as those present at position 9, is selected from: 4-bromophenylalanine. Data is presented herein which shows alteration of the Tyr 9 proteolytic recognition point (see Table 9).

In a yet further embodiment, the non-natural amino acid residues, such as those present at position 11, is selected from: tert-butylglycine. Data is presented herein which shows enhancement of activity and strongly protects the vicinal amino acid backbone from proteolytic hydrolysis by steric obstruction (see Table 9).

In one embodiment, the modified derivative comprises a plurality of the above mentioned modifications, such as 2, 3, 4 or 5 or more modifications. In a further embodiment, the modified derivative comprises 2, 3, 4 or 5 or more of the following modifications, such as all of the following 5 modifications: D-alanine at position 1 and 5, a 1-naphthylalanine at position 4, a 4-bromophenylalanine at position 9 and a tert-butylglycine at position 11. Data is presented herein which shows that this multi-substitution (17-69-07-N252; 17-69-07-N244 and 17-69-07-N255) is tolerated in concert with potency which is superior to wildtype (see Tables 10-12). In a yet further embodiment, the modified derivative comprises the following modifications: D-alanine at position 1 and 5, a 1-naphthylalanine at position 4 and a tert-butylglycine at position 11. Data is presented herein which shows that this multi-substitution (17-69-07-N239) is tolerated in concert with potency which is superior to wildtype (see Table 11).

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In a further embodiment, the amino acid residue at position 1 is substituted for a D-amino acid, such as D-alanine. Data is presented herein which demonstrates retention of potency without the consequent degradation (see Table 6).

In a further embodiment, the amino acid residue at position 5 is substituted for a D-amino acid, such as D-alanine or D-arginine. Data is presented herein which demonstrates retention of potency without the consequent degradation (see Table 7).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled compounds of the invention, i.e. compounds of formula (I), wherein one or more atoms are replaced by atoms having the same atomic number, but an atomic mass or mass number different from the atomic mass or mass number usually found in nature, and compounds of formula (I), wherein metal chelating groups are attached (termed "effector") that are capable of holding relevant (radio)isotopes, and compounds of formula (I), wherein certain functional groups are covalently replaced with relevant (radio)isotopes or isotopically labelled functional groups.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled compounds of formula (I), for example, those incorporating a radioactive isotope, are useful in drug and/or substrate tissue distribution studies, and to clinically assess the presence and/or absence of the MT1-MMP target on diseased tissues such as tumours and elsewhere. The compounds of formula (I) can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Incorporation of isotopes into metal chelating effector groups, such as $^{64}$Cu, $^{67}$Ga, $^{68}$Ga, and $^{177}$Lu can be useful for visualizing tumour specific antigens employing PET or SPECT imaging. In particular, such biodistribution data is presented herein in Example 3.

Incorporation of isotopes into metal chelating effector groups, such as, but not limited to $^{90}$Y, $^{177}$Lu, and $^{213}$Bi, can present the option of targeted radiotherapy, whereby metal-chelator-bearing compounds of formula (I) carry the therapeutic radionuclide towards the target protein and site of action.

Isotopically-labeled compounds of formula (I) can generally be prepared by conventional techniques known to those skilled in the art or by processes analogous to those described in the accompanying Examples using an appropriate isotopically-labeled reagent in place of the non-labeled reagent previously employed.

Binding Activity

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore multispecific. Suitably, they bind to two targets, and are dual specific. The binding may be independent, which would mean that the binding sites for the targets on the peptide are not structurally hindered by the binding of one or other of the targets. In this case, both targets can be bound independently. More generally, it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific due to the absence of selective pressure towards bispecificity. The loop length in the bicyclic peptide may be decisive in providing a tailored binding surface such that good target and orthologue cross-reactivity can be obtained, while maintaining high selectivity towards less related homologues.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. Preferably, the molecular scaffold comprises at least three attachment points for the peptide, referred to as scaffold reactive groups. These groups are capable of reacting with the cysteine residues ($C_i$, $C_{ii}$, and $C_{iii}$) on the peptide to form a covalent bond. They do not merely form a disulphide bond, which is subject to reductive cleavage and concomitant disintegration of the molecule, but form stable, covalent thioether linkages. Preferred structures for molecular scaffolds are described below.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as temazepam.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-tris(bromomethyl)benzene ('TBMB'), or a derivative thereof.

In one embodiment, the molecular scaffold is 2,4,6-tris (bromomethyl)mesitylene. This molecule is similar to 1,3, 5-tris(bromomethyl)benzene but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides. Examples of maleimides which may be used as molecular scaffolds in the invention include: tris-(2-maleimidoethyl) amine, tris-(2-maleimidoethyl)benzene, tris-(maleimido) benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance. Such effectors, when complexed with said radioisotopes, can present useful agents for cancer therapy. Suitable examples include DOTA, NOTA, EDTA, DTPA, HEHA, SarAr and others (Targeted Radionuclide therapy, Tod Speer, Wolters/Kluver Lippincott Williams & Wilkins, 2011).

Possible effector groups also include enzymes, for instance such as carboxypeptidase G2 for use in enzyme/ prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

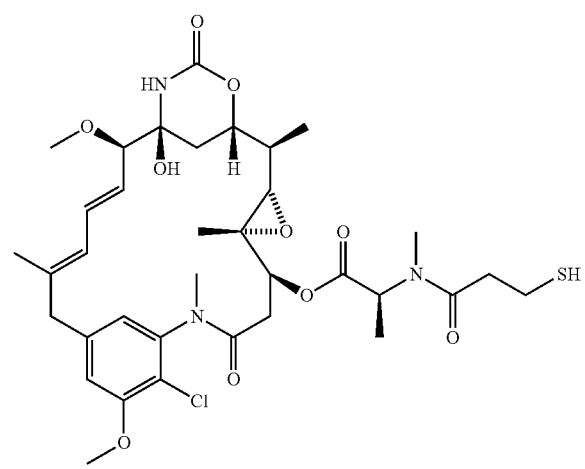

Monomethyl auristatin E (MMAE) is a synthetic antineoplastic agent and has the following structure:

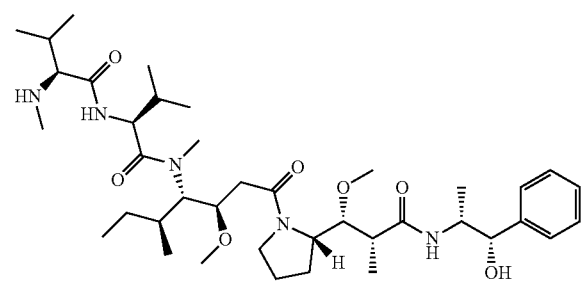 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Data is presented herein in Examples 4 and 5 which demonstrates the effects of peptide ligands conjugated to toxins containing DM1 or MMAE.

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

Thus, in one embodiment, the cytotoxic agent is a maytansinoid selected from a compound of formula (II):

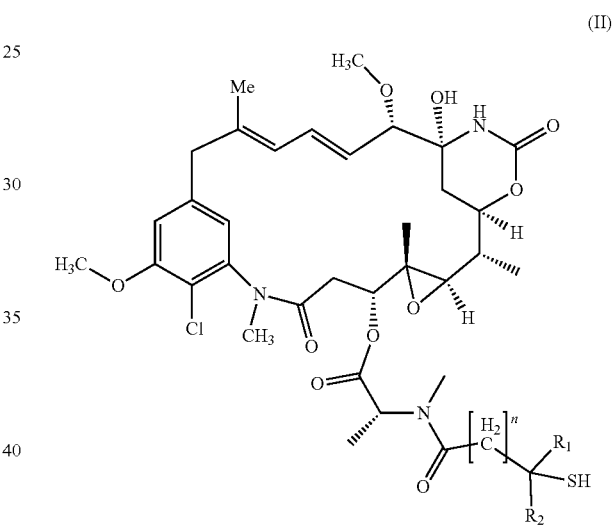

wherein n represents an integer selected from 1 to 10; and
$R_1$ and $R_2$ independently represent hydrogen, $C_{1-6}$ alkyl or a carbocyclyl or heterocyclyl group.

The term $C_{1-6}$alkyl as used herein refers to a linear or branched saturated hydrocarbon group containing from 1 to 6 carbon atoms, respectively. Examples of such groups include methyl, ethyl, n-propyl, isopropyl, n-butyl, isobutyl, sec-butyl, tert butyl, n-pentyl, isopentyl, neopentyl or hexyl and the like.

The term "heterocyclyl" and "carbocyclyl" as used herein shall, unless the context indicates otherwise, include both aromatic and non-aromatic ring systems. Thus, for example, the term "heterocyclyl group" and "carbocyclyl group" include within their scope aromatic, non-aromatic, unsaturated, partially saturated and fully saturated carbocyclyl or heterocyclyl ring systems. In general, unless the context indicates otherwise, such groups may be monocyclic or bicyclic (including fused and bridged bicyclic groups) and may contain, for example, 3 to 12 ring members, more usually 5 to 10 ring members.

In one embodiment of the compound of formula (II), $R_1$ and $R_2$ independently represent hydrogen or methyl.

In one embodiment of the compound of formula (II), n represents 1 and $R_1$ and $R_2$ both represent hydrogen (i.e. the maytansine derivative DM1).

In an alternative embodiment of the compound of formula (II), n represents 2, $R_1$ represents hydrogen and $R_2$ represents a methyl group (i.e. the maytansine derivative DM3).

In one embodiment of the compound of formula (II), n represents 2 and $R_1$ and $R_2$ both represent methyl groups (i.e. the maytansine derivative DM4).

It will be appreciated that the cytotoxic agent of formula (II) can form a disulphide bond, and in a conjugate structure with a bicyclic peptide of formula (I), the disulphide connectivity between the thiol-toxin (II) and thiol-bicycle peptide (III) is introduced through several possible synthetic schemes, two being described in Scheme II or Scheme III.

In one embodiment, the bicyclic peptide component of the conjugate has the structure shown in formula (III):

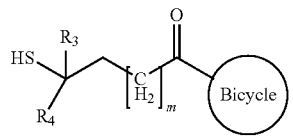

(III)

wherein m represents an integer selected from 0 to 10, and $R_3$ and $R_4$ independently represent hydrogen, $C_{1-6}$ alkyl or a carbocyclyl or heterocyclyl group.

In one embodiment of the compound of formula (III), $R_3$ and $R_4$ independently represent hydrogen or methyl.

Compounds of formula (III) where $R_3$ and $R_4$ are both hydrogen are considered unhindered and compounds of formula (III) where one or all of $R_3$ and $R_4$ represent methyl are considered hindered.

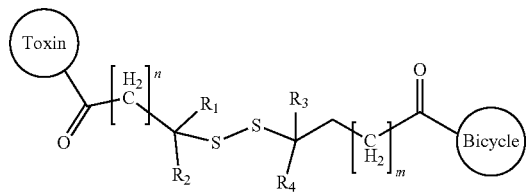

(IV)

wherein $R_1$, $R_2$, $R_3$ and $R_4$ represent hydrogen, $C_{1-6}$ alkyl or a carbocyclyl or heterocyclyl group;

Toxin refers to any suitable cytotoxic agent defined herein;

Bicycle represents any suitable bicyclic peptide defined herein;

n represents an integer selected from 1 to 10; and m represents an integer selected from 0 to 10.

In one embodiment, $R_1$, $R_2$, $R_3$ and $R_4$ represent hydrogen or methyl.

When $R_1$, $R_2$, $R_3$ and $R_4$ are each hydrogen, the disulphide bond is least hindered and most susceptible to reduction. When $R_1$, $R_2$, $R_3$ and $R_4$ are each methyl, the disulphide bond is most hindered and least susceptible to reduction. Partial substitutions of hydrogen and methyl yield a gradual increase in resistance to reduction, and concomitant cleavage and release of toxin.

In one embodiment, the toxin of compound (IV) is a maytansine and the conjugate comprises a compound of formula (V):

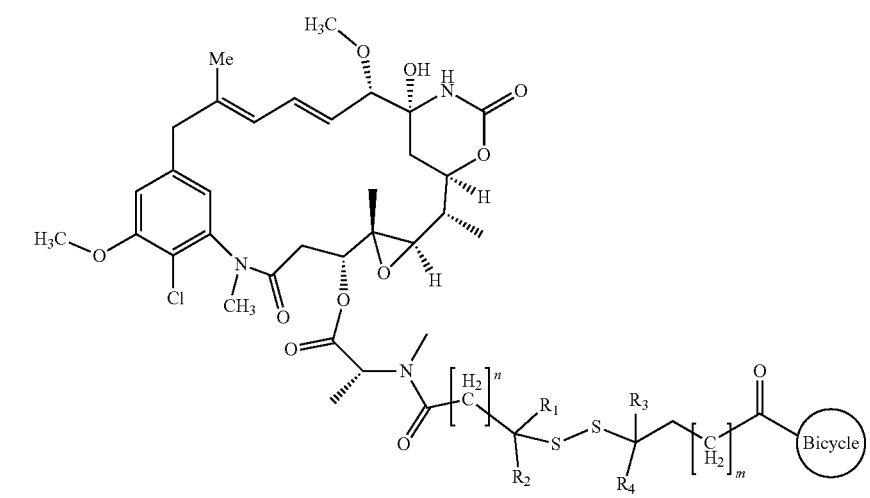

(V)

It will be appreciated that the bicyclic peptide of formula (III) can form a disulphide bond, and in a conjugate structure with a cytotoxic agent of formula (II), the disulphide connectivity between the thiol-toxin (II) and thiol-bicycle peptide (III) is introduced through several possible synthetic schemes, one being described in Scheme II.

In one embodiment, the cytotoxic agent is linked to the bicyclic peptide by a linker defined in formula (IV):

wherein $R_1$, $R_2$, $R_3$ and $R_4$ represent hydrogen, $C_{1-6}$ alkyl or a carbocyclyl or heterocyclyl group;

Bicycle represents any suitable bicyclic peptide as defined herein;

n represents an integer selected from 1 to 10; and m represents an integer selected from 0 to 10.

In a further embodiment of the compound of formula (V), n represents 1 and $R_1$, $R_2$, $R_3$ and $R_4$ each represent hydrogen, i.e. a compound of formula $(V)^a$:

(V)$^a$

The BDC of formula (V)$^a$ is known as BT17BDC-17. The unhindered disulphide in the BDC BT17BDC-17 is the equivalent of BT17BDC-9, whereby the difference resides in the bicyclic peptide portion: BT17BDC-9 employs the non-stabilised sequence (17-69-07-N219), while BT17BDC-17 employs the stabilised bicyclic peptide counterpart (17-69-07-N241) which is amide-bonded to the toxin-disulphide construct. This non-hindered derivative of the maytansine with n=1 is termed DM1.

In a further embodiment of the compound of formula (V), n represents 1, $R_1$ represents methyl and $R_2$, $R_3$ and $R_4$ each represent hydrogen, i.e. a compound of formula (V)$^b$:

(V)$^b$

The BDC of formula (V)$^b$ is known as BT17BDC-18 and contains a single hindering methyl group on the bicyclic peptide side, and in the antibody drug conjugate context produces a 7-fold reduction in its sensitivity to a reducing agent such as dithiothreitol (compared to the non-hindered disulphide) (Kellogg et al (2011) Bioconjugate Chemistry, 22, 717). The reduced sensitivity to reduction is correlated with a lower toxin release rate. This non-hindered derivative of the maytansine with n=1 is termed DM1. BT17BDC-18 employs the stabilised bicyclic peptide counterpart (17-69-07-N241) which is amide-bonded to the toxin-disulphide construct.

In a further embodiment of the compound of formula (V), n represents 2, $R_1$ and $R_2$ both represent hydrogen and $R_3$ and $R_4$ both represent methyl, i.e. a compound of formula (V)$^c$:

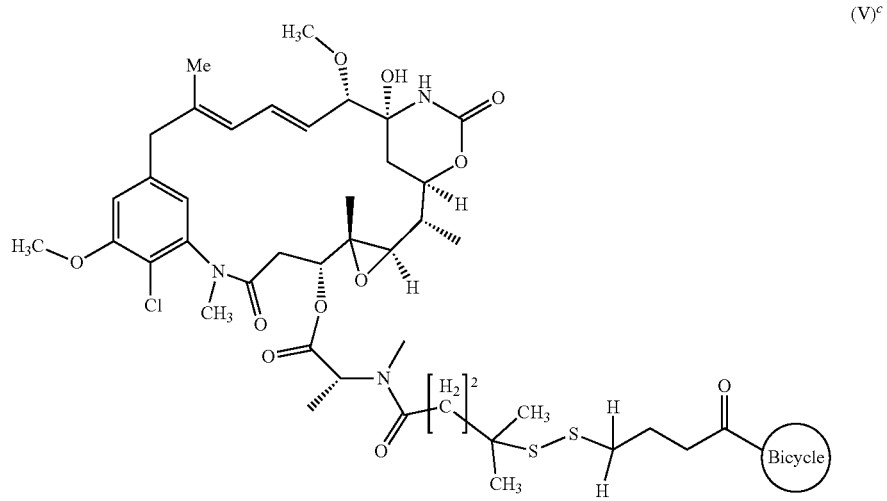

(V)$^c$

The BDC of formula (V)$^c$ is known as BT17BDC-19 and contains two hindering methyl groups on the maytansine side, and in the antibody drug conjugate context produces a 14-fold reduction in its sensitivity to a reducing agent such as dithiothreitol. The reduced sensitivity to reduction is correlated with a lower toxin release rate. This hindered derivative of the maytansine with n=2 is termed DM4. BT17BDC-19 employs the stabilised bicyclic peptide counterpart (17-69-07-N241) which is amide-bonded to the toxin-disulphide construct.

In a further embodiment of the compound of formula (V), n represents 2, $R_1$ and $R_3$ both represent methyl and $R_2$ and $R_4$ both represent hydrogen, i.e. a compound of formula (V)$^d$:

BT17BDC-20 employs the stabilised bicyclic peptide counterpart (17-69-07-N241) which is amide-bonded to the toxin-disulphide construct.

Indeed, in the context of antibody drug conjugates, the balance of efficacy versus tolerability in the animal model showed that its optimum is associated with some level of hindrance, i.e. that of DM4 (Kellogg et al (2011) Bioconjugate Chemistry, 22, 717) which is present as such also in BT17BDC-19.

In one embodiment, the conjugate is selected from BT17BDC-9, BT17BDC-17 (Compound of formula (V)$^a$), BT17BDC-18 (Compound of formula (V)$^b$), BT17BDC-19 (Compound of formula (V)$^c$) and BT17BDC-20 (Compound of formula (V)$^d$). Data is presented in Example 5 and Tables (V)$^d$

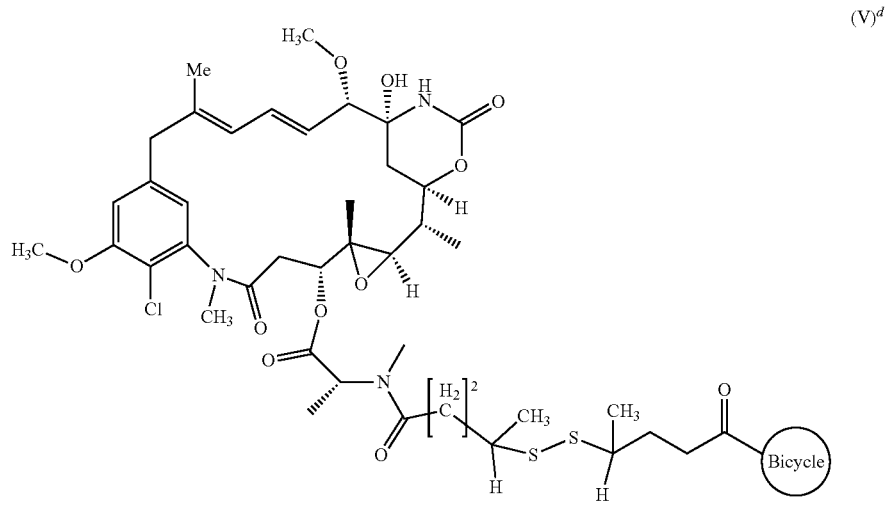

The BDC of formula (V)$^d$ is known as BT17BDC-20 and contains one hindering methyl group on the maytansine side, and one hindering methyl group on the bicycle peptide side, and in the antibody drug conjugate context produces a 170-fold reduction in its sensitivity to a reducing agent such as dithiothreitol. The reduced sensitivity to reduction is correlated with a lower toxin release rate. This hindered derivative of the maytansine with n=2 is termed DM3.

16 and 17 which demonstrate the beneficial properties of BT17BDC-9, BT17BDC-17, BT17BDC-18, BT17BDC-19 and BT17BDC-20.

In a further embodiment, the conjugate is selected from BT17BDC-9, BT17BDC-17 (Compound of formula (V)$^a$), BT17BDC-18 (Compound of formula (V)$^b$) and BT17BDC-19 (Compound of formula (V)$^c$). Data is presented in Example 5 and Tables 16 and 17 which demonstrates that these conjugates were considered suitable molecules for use in targeted cancer therapy.

In a further embodiment, the conjugate is selected from BT17BDC-17 (Compound of formula (V)$^a$), BT17BDC-18 (Compound of formula (V)$^b$) and BT17BDC-19 (Compound of formula (V)$^c$). Data is presented in Example 5 and Tables 16 and 17 which demonstrates that these conjugates are considered suitable molecules for use in targeted cancer therapy and are well tolerated at efficacious doses.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci U S A. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

According to a further aspect of the invention, there is provided a process for preparing a drug conjugate as defined herein which comprises the synthetic route described in any one of Schemes I, II or III.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as high affinity binders of membrane type 1 metalloprotease (MT1-MMP, also known as MMP14). MT1-MMP is a transmembrane metalloprotease that plays a major role in the extracellular matrix remodeling, directly by degrading several of its components and indirectly by activating pro-MMP2. MT1-MMP is crucial for tumor angiogenesis (Sounni et al (2002) FASEB J. 16(6), 555-564) and is over-expressed on a variety of solid tumours, therefore the MT1-MMP-binding bicycle peptides of the present invention have particular utility in the targeted treatment of cancer, in particular solid tumours such as non-small cell lung carcinomas. In one embodiment, the bicyclic peptide of the invention is specific for human MT1-MMP. In a further embodiment, the bicyclic peptide of the invention is specific for mouse MT1-MMP. In a yet further embodiment, the bicyclic peptide of the invention is specific for human and mouse MT1-MMP. In a yet further embodiment, the bicyclic peptide of the invention is specific for human, mouse and dog MT1-MMP.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The effector group and conjugates of the peptide ligands of the present invention will typically find use in preventing, suppressing or treating cancer, in particular solid tumours such as non-small cell lung carcinomas.

Thus, according to a further aspect of the invention, there are provided effector groups and drug conjugates of the peptide ligand as defined herein for use in preventing, suppressing or treating cancer, in particular solid tumours such as non-small cell lung carcinomas.

According to a further aspect of the invention, there is provided a method of preventing, suppressing or treating cancer, in particular solid tumours such as non-small cell lung carcinomas which comprises administering to a patient in need thereof an effector group and drug conjugate of the peptide ligand as defined herein.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods
Phage Selections

6×6 bicycle phage libraries were generated as described in Heinis et al (2009), Nat Chem Biol 5(7), 502-507, WO 2009/098450, WO 2013/050615 and WO 2013/050616. Phage display selections were performed using said 6×6 phage library against the biotinylated human MT1-MMP hemopexin domain.

Protein Expression

The MT1-MMP hemopexin-like repeats (also known as the MT1-MMP hemopexin domain), residues Cys319-Gly511 from the human gene, were transiently expressed in HEK293 cells as secreted N-terminally His6-tagged soluble protein, using the pEXPR-IBA42 (IBA) expression vector. Following expression, the protein was purified by Nickel-NTA affinity chromatography followed by gel filtration, and purity was checked by SDS-PAGE. Batch to batch variability was also monitored by fluorescence thermal shift experiments in the presence/absence of a hemopexin domain binding bicycle.

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with the following side chain protecting groups: Arg(Pbf); Asn(Trt); Asp(OtBu); Cys(Trt); Glu(OtBu); Gln(Trt); His(Trt); Lys(Boc); Ser(tBu); Thr(tBu); Trp(Boc); and Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed using 0.37 mmol/gr Fmoc-Rink amide AM resin (AGTC), Fmoc-amino acids were utilised at a four-fold excess, and base was at a four-fold excess with respect to the amino acids. Amino acids were dissolved at 0.2M in DMSO, HCTU at 0.4M in DMF, and DIPEA at 1.6M in N-methylpyrrolidone (Alfa Aesar). Conditions were such that coupling reactions contained between 20 to 50% DMSO in DMF, which reduced aggregation and deletions during the solid phase synthesis and enhanced yields. Coupling times were generally 30 minutes, and deprotection times 2×5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/H$_2$O/iPr$_3$SiH/dithiothreitol for 3 hours. Following cleavage, the spent resin was removed by filtration, and the filtrate was added to 35 mL of diethylether that had been cooled at −80° C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in H$_2$O, supplemented with 0.5 mL of 1 M dithiothreitol, and loaded onto a C8 Luna preparative HPLC column (Phenomenex). Solvents (H$_2$O, acetonitrile) were acidified with 0.1% heptafluorobutyric acid. The gradient ranged from 30-70% acetonitrile in 15 minutes, at a flowrate of 15-20 mL/min, using a Gilson preparative HPLC system. Fractions containing pure linear peptide material (as identified by MALDI) were combined, and modified with 1,3,5-tris(bromomethyl)benzene (TBMB, Sigma). For this, linear peptide was diluted with H$_2$O up to ~35 mL, ~500 µL of 100 mM TBMB in acetonitrile was added, and the reaction was initiated with 5 mL of 1 M NH$_4$HCO$_3$ in H$_2$O. The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

All amino acids, unless noted otherwise, were used in the L-configurations.

DOTA was coupled to the peptide chain during solid phase peptide synthesis using the protected precursor DOTA (tBu)$_3$ (TCI, CAS 137076-54-1).

Non-natural amino acids were incorporated into peptide sequence using the general methods described above.

The list of non-natural amino acid precursors employed herein are summarised in the table below:

| Supplier | Short name | Full chemical name |
|---|---|---|
| AGTC | D-Asp | Fmoc-D-Asp(tBu)—OH |
| Iris Biotech | HPhe | Fmoc-L-Homophenylalanine |
| Alfa Aesar | 5FPhe | Fmoc-pentafluoro-L-phenylalanine |
| PolyPeptide Gropu | 4BrPhe | Fmoc-4-bromo-L-phenylalanine |
| Iris Biotech | B-Ala | Fmoc-beta-Ala-OH |
| Iris Biotech | 3Pal | Fmoc-L-3Pal-OH |
| Iris Biotech | 4Pal | Fmoc-L-4Pal-OH |
| Iris Biotech | D-Pro | Fmoc-D-Pro-OH |
| Merck Novabiochem | Aib | Fmoc-Aib-OH |
| Merck Novabiochem | D-Ala | Fmoc-D-Ala-OH |
| Merck Novabiochem | D-Arg | Fmoc-D-Arg(Pbf)-OH |
| Merck Novabiochem | D-Gln | Fmoc-D-Gln(Trt)-OH |
| Merck Novabiochem | D-His | Fmoc-D-His(Trt)-OH |
| Merck Novabiochem | Hyp | Fmoc-Hyp(tBu)—OH |
| Merck Novabiochem | D-Leu | Fmoc-D-Leu-OH |

| Supplier | Short name | Full chemical name |
|---|---|---|
| Merck Novabiochem | HArg | Fmoc-L-HArg(Boc)2-OH |
| Peptech Corporation | 4,4-BPAl | Fmoc-L-4,4'-Biphenylalanine |
| Peptech Corporation | 3,3-DPA | Fmoc-L-3,3-Diphenylalanine |
| Peptech Corporation | Dpg | Fmoc-Dipropylglycine |
| Peptech Corporation | 1NAl | Fmoc-L-1-Naphthylalanine |

-continued

| Supplier | Short name | Full chemical name |
|---|---|---|
| Peptech Corporation | 2NAl | Fmoc-L-2-Naphthylalanine |
| Peptech Corporation | Pip | Fmoc-L-Pipecolic acid |
| Polypeptide Group | Aze | Fmoc-L-azetidine-2-carboxylic acid |
| Polypeptide Group | Cha | Fmoc-beta-cyclohexyl-L-alanine |
| Polypeptide Group | 4FluoPro | (2S,4R)-Fmoc-4-fluoro-pyrrolidine-2-carboxylic acid |
| AGTC | D-Asp | Fmoc-D-Asp(tBu)—OH |
| Merck | tBuGly | Fmoc-α-tert-butylglycine |
| Iris Biotech | Chg | Fmoc-L-cyclohexylglycine |
| Fluorochem | Phg | Fmoc-Phenylglycine-OH |
| Iris Biotech | 3Pal | Fmoc-L-3Pal-OH |
| Iris Biotech | 4Pal | Fmoc-L-4Pal-OH |
| Merck Novabiochem | D-Leu | Fmoc-D-Leu-OH |
| Merck Novabiochem | HArg | Fmoc-L-HArg(Boc)2-OH |
| Polypeptide Group | 3,4 DCPhe | Fmoc-3,4-dichloro-L-phenylalanine |
| Polypeptide Group | Cha | Fmoc-beta-cyclohexyl-L-alanine |

Peptides used for the pharmacokinetic studies were lyophilised from 0.1% TFA in water to afford the TFA salts or free acids of the compounds.

Synthesis of BDCs Using 17-69-07-N219 as a Precursor Bicyclic Peptide

Two Bicycle Drug Conjugates (BDC) were synthesised, using 17-69-07-N219 as a precursor peptide. The activated vcMMAE or disulphide-DM1 constructs (dissolved in DMSO) were directly conjugated at 1.4× excess with 17-69-07-N219 in aqueous conditions (100 sodium phosphate pH8) (see Schemes I and II). Concentrations were at 9 mg/mL peptide or higher. The reaction was followed by LC/MS and judged complete after 3.5 hours. This was followed by standard reverse phase purification using a C18 semi-preparative column. Fractions at purity greater than 95% were isolated and lyophilised. The materials did not contain measurable quantities of free toxin. For the in vitro and in vivo studies, lyophilised powders were taken up as concentrated DMSO stocks (100 mg/mL), and diluted in the appropriate buffer for further use.

Synthesis of BDCs Using 17-69-07-N241 as a Precursor Bicyclic Peptide

For synthesis of BT17BDC-17, BT17BDC-18, BT17BDC-19 and BT17BDC-20, the following N-hydroxy succinimide esters (NHS esters) of disulphide maytansinoids were used:

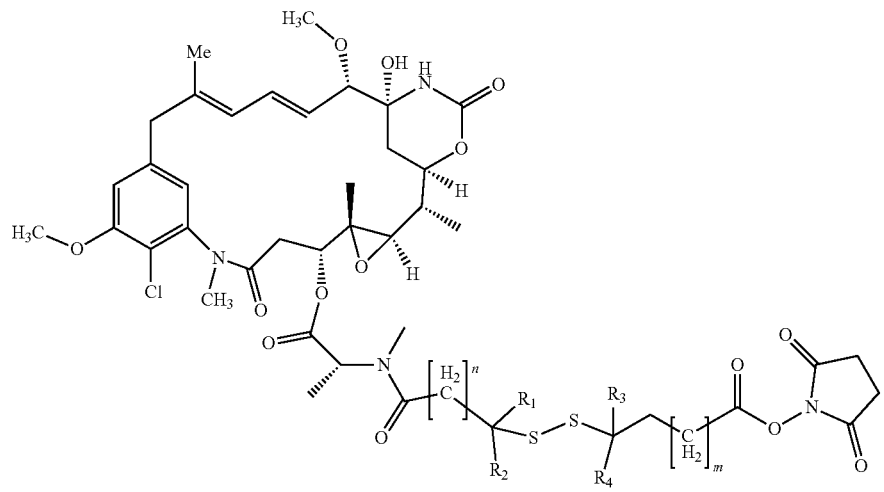

wherein $R_1$, $R_2$, $R_3$, $R_4$, m and n are as described hereinbefore for compounds of formula $(V)^a$, $(V)^b$, $(V)^c$, $(V)^d$ for BT17BDC-17, BT17BDC-18, BT17BDC-19 and BT17BDC-20, respectively.

BT17BDC-18 was further synthesised through an alternative route, as described below and in Scheme III. Here, 17-69-07-N277 was synthesised by reacting 17-69-07-N241 with SPP (N-succinimidyl 4-(2-pyridyldithio)pentanoate) in DMSO. Concentrations of 17-69-07-N241 were 10 mM or higher, with a 1.3 fold excess of SPP, and a 20-fold excess of diisopropylethylamine, at room temperature. The reaction was judged complete after 1 hour, as judged by LCMS. Purification was performed by reverse phase as described above. Appropriate fractions were lyophilised.

17-69-07-N277 was disulphide exchanged with 1.15 equivalents of DM1 (as the free thiol), in semi aqueous conditions (50% dimethylacetamide and 50% 100 mM sodium acetate pH 5.0 supplemented with 2 mM EDTA) for 21 hours at room temperature under a nitrogen gas blanket. Concentrations of 17-69-07-N277 in the reaction were at 10 mM or higher. This was followed by standard reverse phase purification using a C18 semi-preparative column. Fractions at purity greater than 95% were isolated and lyophilised. The materials did not contain measurable quantities of free toxin. For the in vitro and in vivo studies, lyophilised powders were solubilised in aqueous formulation as described above, or taken up directly in the appropriate buffer.

Dissociation Rate Constant Determination of Bicyclic Binders to MT1-MMP Direct Binding Fluorescence Polarisation (Anisotropy) Assays Direct Binding Fluorescence Polarisation or Anisotropy Assays are performed by titrating a constant concentration of fluorescent tracer (here, the fluoresceinated bicyclic peptide to be studied) with its binding partner (here, the MT1-MMP hemopexin domain). As the concentration of binding partner increases during the titration, the polarisation signal changes in proportion to the fraction of bound and unbound material. This allows determination of dissociation rates (Kd) quantitatively. Assay data can be fit using standard ligand binding equations.

Typically, concentrations of the tracer are ideally well below the Kd of the tracer:titrant pair, and concentrations chosen are usually at ~1 nM or less. The titrant (binding partner) concentration is varied from 0.1 nM up to typically 5 µM. The range is chosen such that the maximum change in fluorescent polarisation can be observed. Buffers employed are phosphate buffered saline in the presence of 0.01% Tween. Experiments were run in black 384 well low-bind/low volume plates (Corning 3820), and the fluorescent polarisation signal was measured using a BMG Pherastar FS plate reader.

Fluorescent tracers referred to in the text are bicyclic peptides that have been fluoresceinated using 5,6-carboxyfluorescein. Fluoresceination may be performed on the N-terminal amino group of the peptide, which is separated from the bicycle core sequence by a sarcosine spacer (usually Sar5). This can be done during Fmoc solid phase synthesis or post-synthetically (after cyclisation with TBMB and purification) if the N-terminal amino group is unique to the peptide. Fluoresceination can also be performed on the C-terminus, usually on a Lysine introduced as the first C-terminal residue, which is then separated from the bicycle core sequence by a sarcosine spacer (usually Sar6). Thus, N-terminal tracers can have a molecular format described as Fluo-Gly-Sar5-A(BicycleCoreSequence), and (BicycleCoreSequence)-A-Sar6-K(Fluo) for a C-terminally fluoresceinated construct. Fluorescent tracers used in the Examples are A-(17-69)-A-Sar6-K(Fluo), A-(17-69-07)-A-Sar6-K(Fluo), and A-(17-69-12)-A-Sar6-K(Fluo). Due to the acidic nature of the 17-69 fluorescent peptides, they were typically prepared as concentrated DMSO stocks, from which dilution were prepared in 100 mM Tris pH 8 buffer.
Competition Assays Using Fluorescence Polarisation (Anisotropy)

Due to their high affinities to the MT1-MMP Hemopexin domain (PEX), the fluoresceinated derivatives of 17-69-07 and 17-69-12 (denoted as 17-69-07-N040 and 17-69-12-N005, respectively) can be used for competition experiments (using FP for detection). Here, a pre-formed complex of PEX with the fluorescent PEX-binding tracer is titrated with free, non-fluoresceinated bicyclic peptide. Since all 17-69-based peptides are expected to bind at the same site, the titrant will displace the fluorescent tracer from PEX. Dissociation of the complex can be measured quantitatively, and the Kd of the competitor (titrant) to the target protein determined. The advantage of the competition method is that the affinities of non-fluoresceinated bicyclic peptides can be determined accurately and rapidly.

Concentrations of tracer are usually at the Kd or below (here, 1 nM), and the binding protein (here, hemopexin of MT1-MMP) is at a 15-fold excess such that >90% of the tracer is bound. Subsequently, the non-fluorescent competitor bicyclic peptide (usually just the bicycle core sequence) is titrated, such that it displaces the fluorescent tracer from the target protein. The displacement of the tracer is measured and associated with a drop in fluorescence polarisation. The drop in fluorescence polarisation is proportional to the fraction of target protein bound with the non-fluorescent titrant, and thus is a measure of the affinity of titrant to target protein.

The raw data is fit to the analytical solution of the cubic equation that describes the equilibria between fluorescent tracer, titrant, and binding protein. The fit requires the value of the affinity of fluorescent tracer to the target protein, which can be determined separately by direct binding FP experiments (see previous section). The curve fitting was performed using Sigmaplot 12.0 and used an adapted version of the equation described by Zhi-Xin Wang (FEBS Letters 360 (1995) 111-114).
Plasma Stability Profiling
Method #1:

A rapid plasma stability profiling assay was developed that employed mass spectrometric detection (MALDI-TOF, Voyager DE, Applied Biosystems) of the parent mass as well as plasma-protease induced fragments thereof. By assessing the nature of the fragments, preferred cleavage sites can be determined. Here, a 1-1.5 mM peptide stock (in DMSO) was directly diluted into mouse/rat/human plasma (Sera labs, using citrate as anticoagulant), giving a final concentration of 50 µM peptide, and incubated for up to 48 hrs at 37° C. 5 µL samples were taken at appropriate time points and frozen at −80° C. For analysis, the samples were defrosted, mixed with 25 µL of 3:3:1 acetonitrile:methanol:water, and centrifuged at 13 k for 5 min. 5 µL of the peptide-containing supernatant was aspirated and mixed with 30 mM ammonium bicarbonate in a 1:1 mixture of acetonitrile:$H_2O$. 1 µL of this was then spotted on the MALDI plate, dried, and Matrix (alpha-cyanocinnamic acid, Sigma, prepared as a saturated solution in 1:1 acetonitrile:water containing 0.1% trifluoroacetic acid) was layered over the sample (1 µL), dried and analysed using the MALDI TOF. It should be noted that this is a qualitative assay serves to detect comparative changes in plasma stability between different bicycle peptide sequences, and functions as an excellent tool to determine preferred cleavage sites.
Method #2

To obtain plasma stability of bicyclic peptides quantitatively, peptide stock solutions (200 µM in DMSO) were mixed with plasma (human or mouse), such that final concentrations were 10 µM. 40 µL samples were taken periodically up to 8 hrs and frozen at −80° C. Prior to LC-MS analysis, samples were defrosted, and mixed with 3 volumes (here, 120 µL) of 1:1 acetonitrile/MeOH water. The milky suspensions were centrifuged for 30 min at 13000 rpm, and peptide-containing supernatants were quantitated for doubly/triply charged species and MS/MS fragments thereof using a Waters Xevo TQ-D instrument, while using a plasma extracted standard curve of the same peptides as a reference. The half-life of degradation in plasma was used to assess the comparative stability of the molecules.
Pharmacokinetics of 17-69-07 in Mouse, Identification of Metabolites
Pharmacokinetics of 17-69-07-N004

Mouse pharmacokinetics were acquired using bicyclic peptide 17-69-04-N004, which was dosed to one group of 12 male CD1 mice as a single intravenous, 5.925 mg/kg doses as a 5 mL/kg bolus of a 1.19 mg/mL solution. Formulated solutions were prepared from 100 µL of a 23.7 mg/mL DMSO stock, which was diluted with 1.9 mL of phosphate buffered saline immediately prior to dosing, resulting in a vehicle consisting of 5% DMSO in PBS at pH 7.4. Blood samples were taken from two animals per time-point, via cardiac puncture under terminal anaesthesia, at 0.08, 0.5, 1, 2 and 4 hours post-dose, and transferred to EDTA tubes for plasma generation. Plasma samples were immediately frozen at −20 C. For analysis, samples were thawed rapidly and 50 µL aliquots were treated with 3 volumes of extraction solvent (2:9:9 mixture of 10 mM ammonium bicarbonate, pH 8, acetonitrile and methanol, containing an analytical internal standard). Precipitated proteins were removed by centrifugation and the supernatant was analysed by LC-MS/MS. Quantification of the samples was by reference to a calibration line prepared in control mouse plasma. Pharmacokinetic parameters were determined by non-compartmental analysis using the software package PK Solutions 2.0 from Summit Research Services.

Definition of Terms

Cmax: Maximum measured concentration;
Tmax: Time at which maximum concentration was measured;
AUC 0-t: Area under the plasma drug concentration/time curve from 0 minutes to last quantifiable data point; and
AUC 0-∞: Area under the plasma drug concentration/time curve from 0 minutes extrapolated beyond the final data point based on the terminal half-life.

Identification of Bicyclic Peptide Metabolites in Mouse Plasma

Three plasma samples were available to be used (0.5, 1 and 2 hrs) for analysis of potential mouse in vivo metabolites of 17-69-07-N004. Analysis was performed by HPLC-MS and HPLC-MS/MS with a LTQ Orbitrap XL Mass Spectrometer. The approach to look for peptidic metabolites in the blood circulation was to calculate the exact mass (10 ppm window) of assumed metabolites (addition of 1 or 2 water (+18, +36) for cleavage of loop 1 and/or loop 2, respectively; thereafter loss of single amino acids or loss of amino acid stretches from loop 1 and/or loop 2). Secondly a manual search was performed by comparing the total ion chromatograms with blank mouse plasma.

Efficacy of BT17BDC-1 and BT17BDC-9 in HT-1080 Xenograft Mice.

Balb/c nude mice bearing subcutaneous HT-1080 xenograft tumours were treated with BDCs or vehicle (PBS). BDCs were dosed 3 times weekly for 2 weeks, dosing initiated when tumours measured approx. 150-200 mm$^3$. Mice were monitored, and measurements of tumour volume and body weight recorded 3 times a week.

Example 1: Identification of Bicyclic Peptides with High Affinity Using MT1-MMP Hemopexin Domain Employing previously established methods for generating bicyclic peptide phage libraries, selections were performed against the human hemopexin domain of MT1-MMP. Following three rounds of selections from a naïve library employing successively reduced concentrations of target, sequencing was performed on the outputs. Bicyclic peptide 17-69 (CKNRGFGCEDFYDIC) (SEQ ID NO: 16) was identified as one the most abundant sequence outputs, and qualitative binding to the target was verified by Alphascreen.

Three small phage libraries were generated providing full sequence coverage of each of 3 portions of the 17-69 sequence. These three libraries were subjected to two rounds of selections against hemopexin protein. Interestingly, the most promising sequencing outputs were 5×6 bicyclic peptides, while the starting libraries were of the 6×6 format. It is likely that the shorter loop length was selected due to a higher affinity of the bicyclic peptide to the target protein. Shorter loop lengths result from incorrectly synthesised primers that are incorporated during the construction of the phage libraries.

The main sequencing output was the peptide 17-69-07, which has the sequence CYNEFGCEDFYDIC (SEQ ID NO: 2).

Based on the observation that a 5×6 format appeared most fruitful, and that distinction between the 5×6 binders was required, two more libraries were generated testing deliberate truncations of the first loop which generated bicyclic peptides 17-69-02, 17-69-03, 17-69-04 and 17-69-12. These are contained within sequences disclosed in FIG. 8.

A trend for certain residues was visible, although the binding assay was not able to distinguish between the best binders as they had reached the assay ceiling.

The most frequently occurring sequences were assayed for Hemopexin binding using the alpha screen, where all signals were high compared to the original 17-69 sequence (see Table 1 and FIG. 14):

Table 1: Hemopexin Binding Assay Using the Bicyclic Peptides of the Invention

| Name | Format | Sequence |
|---|---|---|
| 17-69 | 6 × 6 | CKNRGFGCEDFYDIC (SEQ ID NO: 16) |
| 17-69-02 | 5 × 6 | CFGEFGCEDFYDIC (SEQ ID NO: 11) |
| 17-69-03 | 5 × 6 | CVNEFGCEDFYDIC (SEQ ID NO: 12) |
| 17-69-04 | 5 × 6 | CFNEFGCEDFYDIC (SEQ ID NO: 13) |
| 17-69-07 | 5 × 6 | CYNEFGCEDFYDIC (SEQ ID NO: 2) |
| 17-69-12 | 5 × 6 | CMNQFGCEDFYDIC (SEQ ID NO: 10) |

Figure 14:
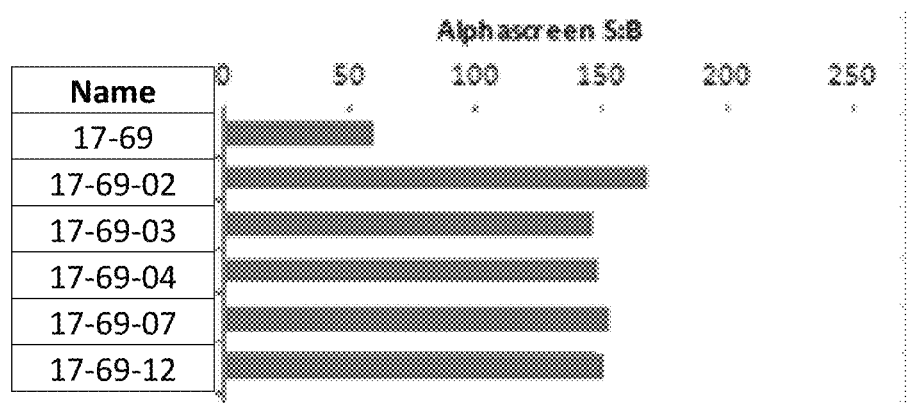
FIG. 14: An illustration of signals in an assay for Hemopexin binding using the alpha screen.

As all of the 17-69-based affinity-mature clones produced signals that were near the assay ceiling, the plot shown in FIG. 14 does not allow unequivocal identification of the best clones. Some of the peptides were therefore synthesised as the fluoresceinated derivatives (17-69, 17-69-07 and 17-69-12), and used for direct binding fluorescent polarisation (FP) experiments. Here, the fluorescein is separated by a linker (usually Sar6) from the bicyclic sequence, either N or C-terminal to the core sequence (Table 2).

TABLE 2

Results of Direct Binding Fluorescent Polarisation (FP) Experiments

| Peptide Code | Molecular Format | FP Method | Tracer | Kd (nM) |
|---|---|---|---|---|
| 17-69-N004 | A-(17-69)-A-Sar6-K(Fl) | Direct Binding | A-(17-69)-A-Sar6-K(Fluorescein) | 692 |
| 17-69-02-N001 | A-(17-69-02)-A | Competition | A-(17-69-07)-A-Sar6-K(Fluorescein) | 191 |
| 17-69-03-N001 | A-(17-69-03)-A | Competition | A-(17-69-07)-A-Sar6-K(Fluorescein) | 16.7 |

TABLE 2-continued

Results of Direct Binding Fluorescent Polarisation (FP) Experiments

| Peptide Code | Molecular Format | FP Method | Tracer | Kd (nM) |
|---|---|---|---|---|
| 17-69-12-N005 | A-(17-69-12)-A-Sar6-K(Fl) | Direct Binding | A-(17-69-07)-A-Sar6-K(Fluorescein) | 3.1 |
| 17-69-07-N040 | A-(17-69-07)-A-Sar6-K(Fl) | Direct Binding | A-(17-69-07)-A-Sar6-K(Fluorescein) | 0.52 |

The fluoresceinated derivatives of 17-69-07 and 17-69-12 (denoted as 17-69-07-N040 and 17-69-12-N005) showed strong binding with 0.52 and 3.1 nM dissociation rates, respectively. They are markedly improved over the original non-matured 17-69 sequence (17-69-N004). It appears that sequences that contain the 5×6 format induce high affinities within the context of the affinity maturation library.

Due to their high affinities to the MT1-MMP Hemopexin domain (PEX), the fluoresceinated derivatives of 17-69-07 and 17-69-12 (denoted as 17-69-07-N040 and 17-69-12-N005, respectively) were used for subsequent competition experiments (using FP for detection). Here, a pre-formed complex of PEX with the fluorescent PEX-binding tracer is titrated with free, non-fluoresceinated bicyclic peptide. Since all 17-69-based peptides (containing the conserved second loop motif CEDFYDIC; SEQ ID NO: 17) are expected to bind at the same site, the titrant will displace the fluorescent tracer from PEX. Dissociation of the complex can be measured quantitatively, and the Kd of the competitor (titrant) determined. The advantage of the competition method is that the affinities of non-fluoresceinated bicyclic peptides can be determined accurately and rapidly.

In this context, it was important to verify that the 17-69-07 and 17-69-12 core sequences are solely responsible for the high affinity to PEX. Peptides were thus synthesised as variants with N and C-terminal Alanines, thereby closely mimicking the sequence expressed on the phage particle, but lacking the Sar5/6 molecular spacer that was used with the fluoresceinated constructs.

Affinities as determined by competition experiments were almost identical to those obtained with the fluoresceinated derivatives, demonstrating unequivocally that the core bicyclic sequences are responsible for the high affinity binding to PEX (Table 3). Furthermore, the fluoresceinated constructs show that C-terminal linkages of molecular spacers and effector groups (here, as -A-Sar6-K(Fluorescein) are tolerated.

Example 2: Proteolytic Stabilisation of the 17-69-07 Core Sequence

Mouse Plasma Stability of 17-69-07

For therapeutic applications in man, and for pre-clinical assessment in animal species, it is pertinent that a lead bicycle peptide is sufficiently stable in the circulation following intravenous administration. Adequate stability is required such that sufficient levels of bicycle peptide can bind to its target and exert its biological function.

Preclinical models often employ species such as mouse, rat, rabbit and cynomolgus monkey. In the first instance, the bicyclic peptide 17-69-07-N219 was assessed for stability in the presence of mouse plasma using methods described hereinbefore (Method #2). The bicycle core sequence retains the original natural proteinogenic amino acids of the 17-69-07 sequence, and additionally contains an N-terminal molecular spacer that is used for conjugation of effector groups (sequence: G-Sar10-ACYNEFGCEDFYDIC; SEQ ID NO: 20). The affinity of 17-69-07-N219 to PEX was retained in spite of the presence of the molecular spacer (Kd=0.82 nM).

This compound displayed a modest stability in ex vivo mouse plasma, with a half-life of 6 hours (see FIG. 1).
Identification of Ex/In Vivo Proteolytic Cleavage Sites in 17-69-07

In an effort to understand the chemical nature of the degradation of 17-69-07-N219 in mouse plasma, samples were analysed using MALDI-TOF for any potential degradation products. Mass spectra indicated a possible loss of tyrosine, which implicates loop opening (hydrolysis) and removal of Tyr1 in loop 1 and/or Tyr9 in loop2.

A mouse pharmacokinetic (PK) study using the minimal bicyclic peptide 17-69-07-N004 (Ac-CYNEFGCEDFYDIC (SEQ ID NO: 2), which constitutes the minimal core bicyclic peptide of 17-69-07), was conducted in order to establish clearance and elimination rates from the in vivo circu-

TABLE 3

Results of Direct Binding Fluorescent Polarisation (FP) Experiments

| Peptide Code | Molecular Format | Sequence | FP Method | Tracer | Kd (nM) |
|---|---|---|---|---|---|
| 17-69-07-N001 | A-(17-69-07)-A | ACYNEFGCEDFYDICA (SEQ ID NO: 18) | Competition | A-(17-69-12)-A-Sar6-K(Fluorescein) | 1.65 ± 0.29 |
| 17-69-12-N003 | A-(17-69-12)-A | ACMNQFGCEDFYDICA (SEQ ID NO: 19) | Competition | A-(17-69-07)-A-Sar6-K(Fluorescein) | 3.7 ± 2.52 | lation. Resulting blood samples were further analysed, and to analyse plasma samples for any potential proteolytic degradation products of 17-69-07-N004.

Figure 2:
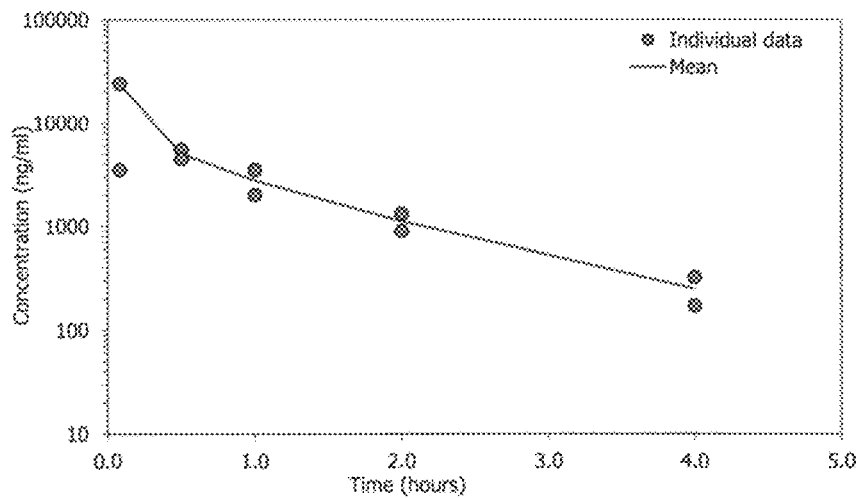
FIG. 2: PK profile of Bicyclic Peptide 17-69-07-N004 in mouse. 2 animals per time point.

The PK profile is indicated in FIG. 2.

TABLE 4

Pharmacokinetic Parameters for 17-69-07-N004

| PK Parameter | Mean |
|---|---|
| Cmax (ng/ml) | 15789 |
| Tmax (min) | 5.0 |
| Distribution Half-life (min) | NC |
| Elimination Half-life (min) | 14 |
| AUC 0-t (µg/ml · min) | 286 |
| AUC 0-∞ (µg/ml · min) | 286 |
| Volume of Distribution based on AUC 0-∞ (L/kg) | 0.4 |
| Clearance based on AUC 0-∞ (ml/min/kg) | 20.7 |
| Time-points for Elim. Half-life regression (min) | 5-60 |

NC: not calculated due to limited data

Table 4 shows that the peptide has an elimination half-life of 14 min, and is cleared at 20.7 mL/min/kg. The clearance rate is greater than the glomerular filtration rate observed in mice (summarised in Qi et al, American Journal of Physiology-Renal Physiology (2004) Vol. 286 no. 3, F590-F596), indicating that the peptide is cleared by additional means, for example proteolysis driven by plasma and endothelial proteases.

To address whether in vivo proteolysis contributes significantly to clearance, plasma samples taken at t=0.5, 1 and 2 hrs were subjected to targeted analysis for bicycle fragments using LC-MS/MS techniques.

Multiple proteolytic metabolites could be identified, and fragments with the most intense signals are listed below in descending order: Ac-$C_i$YNEFGC$_{ii}$EDFYDIC$_{iii}$ (SEQ ID NO: 2):

excision of YNE in loop 1;
excision of YNEF in loop 1 (SEQ ID NO: 21);
excision of YNEFG (SEQ ID NO: 22) in loop 1 (the entire loop is removed);
excision of Y in loop 1 and/or 2;
excision of YD in loop 2;
excision of FYD in loop 2;
excision of YDI in loop 2; and
excision of EDFYDI (SEQ ID NO: 23) in loop 2 (the entire loop is removed).

The top three metabolites were present at medium signal level, while the remaining fragments were only detectable at trace quantities.

Taken together, both ex and in vivo metabolites appear to centre on initial cleavage at or near Tyr 1/9, followed by successive removal of residues in the vicinity. This ultimately leads to removal of either or both loops in their entirety.

Proteolytic Stability and Potency Enhancement of the 17-69-07 Sequence

Approaches to stabilising peptide sequences from proteolytic degradation are numerous (for reviews see Gentilucci et al, Curr. Pharmaceutical Design, (2010), 16, 3185-203, and Nestor et al, Curr. Medicinal Chem (2009), 16, 4399-418), and WO 2009/098450, WO 2013/050615 and WO 2013/050616). Briefly, they comprise substitution of the amino acid that provides a recognition point to the protease (s), alteration of amino acid backbone at the cleavage site (i.e. N-methylation, pseudo peptide bonds etc), steric obstruction of bonds nearby (i.e. µ-substituted amino acids), and inclusion of D-enantiomeric amino acids. Some of these modifications (i.e. N-methylation, D-amino acids) may protect/shield a proteolytic cleavage site from hydrolysis even if they are located up to two residues away from the cleavage site. While it is relatively straight-forward to protect a sequence from proteolytic attack, it is much more challenging to incorporate stabilising changes that do not dramatically alter the potency (and specificity) to the target protein.

From the ex/in vivo proteolytic degradation data of 17-69-07 shown in the previous section, it is clear that Tyr1/9 and residues in the vicinity are potential sites for stabilisation of the bicyclic peptide. A quantitative means to assess successful stabilisation of the peptide is through an increase of its half-life in mouse and human plasma.

In the first instance, eleven derivatives of 17-69-07 were generated where each position was replaced by an alanine (termed "alanine scan"). This type of information advises on the energetic contribution and role of certain residues, and potentially removes proteolytic recognition points.

TABLE 5

Alanine Scan Results

| Peptide code | Molecular Description | Kd (nM) |
|---|---|---|
| 17-69-07-N004 | Ac-(17-69-07) (wildtype) $C_i$YNEFGC$_{ii}$EDFYDIC$_{iii}$ (SEQ ID NO: 2) | 2.47 ± 0.25 |
| 17-69-07-N014 | Ac-(17-69-07) Ala1 | 3.8 |
| 17-69-07-N015 | Ac-(17-69-07) Ala2 | >5000 |
| 17-69-07-N016 | Ac-(17-69-07) Ala3 | 5.1 |
| 17-69-07-N017 | Ac-(17-69-07) Ala4 | 34 |
| 17-69-07-N018 | Ac-(17-69-07) Ala5 | >5000 |
| 17-69-07-N019 | Ac-(17-69-07) Ala6 | >5000 |
| 17-69-07-N020 | Ac-(17-69-07) Ala7 | >5000 |
| 17-69-07-N021 | Ac-(17-69-07) Ala8 | >5000 |
| 17-69-07-N022 | Ac-(17-69-07) Ala9 | >5000 |
| 17-69-07-N023 | Ac-(17-69-07) Ala10 | 11.1 |
| 17-69-07-N024 | Ac-(17-69-07) Ala11 | 8 |

17-69-07-N004 is the wild-type, unmodified peptide containing a capped N-terminus (N-terminally acetylation, termed "Ac"). Some of the Ala substitutions are well-tolerated, especially at positions 1, 3, 4, 10 and 11 within the sequence. As the side chains of these residues are not required for high affinity binding to the target, compounds of formula (I) at these particular sequence positions are defined broadly.

This makes substitution at residue 1 (Tyr 1) a very attractive possibility, as it may remove one of the proteolytic recognition points. The substitution of Gly5 with Ala5 is of interest as the chemical change is minor (addition of methyl group), yet produces a dramatic reduction in potency. It is possible that Gly5 adopts unusual phi/psi angles outside the general Ramachandron chart, and these angles could be potentially induced by D-amino acids. The additional benefit would be stabilisation of the peptide bonds adjacent to this site.

For this reason, a partial D-alanine scan was performed to assess whether they are tolerated with respect to maintenance of potency: Inclusion of D-amino acids in the sequence is highly desirable due to their proteolytically stabilising effect.

TABLE 6

Effect of substituting residues in the first loop with D-Alanines

| Peptide code | Molecular Description | Kd (nM) |
|---|---|---|
| 17-69-07-N004 | Ac-(17-69-07) (wildtype) | 2.47 ± 0.25 |
| 17-69-07-N061 | Ac-(17-69-07) D-Ala1 | 23.6 |
| 17-69-07-N062 | Ac-(17-69-07) D-Ala2 | >5000 |
| 17-69-07-N063 | Ac-(17-69-07) D-Ala3 | 105 n = 1 |
| 17-69-07-N056 | Ac-(17-69-07) D-Ala4 | >5000 |
| 17-69-07-N058 | Ac-(17-69-07) D-Ala5 | 2.37 ± 0.86 |
| 17-69-07-N059 | Ac-(17-69-07) D-Pro5 | >5000 |

D-Ala1 in place of Tyr1 binds at an affinity 10-fold less than wildtype. Nonetheless it is of interest as the proteolytic recognition point Tyr1 is removed and replaced by a stabilising amino acid, without inducing a major loss in potency.

Remarkably, substitution of Gly5 with D-Ala5 is well-tolerated, as the affinity compared to wildtype remains unchanged.

In this context, D-Arg5 is also tolerated (and likely therefore all D-amino acids except D-Pro, see Table 6), which could be of interest if the physico-chemical properties need altering during further development of the molecule (Table 7).

TABLE 7

Effect of substituting residues at position 5

| Peptide code | Molecular Description | Kd (nM) |
|---|---|---|
| 17-69-07-N004 | Ac-(17-69-07) (wildtype) | 2.47 ± 0.25 |
| 17-69-07-N018 | Ac-(17-69-07) Ala5 | >5000 |
| 17-69-07-N058 | Ac-(17-69-07) D-Ala5 | 2.37 ± 0.86 |
| 17-69-07-N120 | Ac-(17-69-07) D-Arg5 | 4.24 ± 1.48 |

Next, due to the phage selection outputs indicating a certain preference for hydrophobic and aromatic amino acids at position 4 of the sequence, a series of derivatives were synthesised incorporating select aromatic amino acids, including the natural tyrosine and tryptophan (Table 8).

TABLE 8

Effect of substituting residues at position 4

| Peptide code | Molecular Description | Kd (nM) |
|---|---|---|
| 17-69-07-N004 | Ac-(17-69-07) (wildtype) | 2.47 ± 0.25 |
| 17-69-07-N057 | Ac-(17-69-07) Tyr4 | 1.78 ± 0.45 |
| 17-69-44-N002 | Ac-(17-69-07) Trp4 | 0.75 ± 0.23 |
| 17-69-07-N067 | Ac-(17-69-07) 1NAl4 | 0.36 ± 0.12 |
| 17-69-07-N068 | Ac-(17-69-07) 2NAl4 | 0.7 ± 0.19 |
| 17-69-07-N065 | Ac-(17-69-07) Chg4 | >5000 |
| 17-69-07-N071 | Ac-(17-69-07) Phg4 | 628 |
| 17-69-07-N072 | Ac-(17-69-07) tBuGly4 | >5000 |
| 17-69-07-N137 | Ac-(17-69-07) 3,4-DCPhe4 | 1.85 ± 2.45 |
| 17-69-07-N139 | Ac-(17-69-07) Cha4 | 362 |
| 17-69-07-N140 | Ac-(17-69-07) HPhe4 | 43.3 |

1Nal: 1-naphthylalanine; 2NAl: 2-naphthylalanine; Chg: cyclohexylglycine, Phg: phenylglycine; tBuGly: tert-butylglycine; 3,4-DCPhe4: 3,4-dichlorophenylalanine; Cha: cyclohexylalanine; and HPhe: homophenylalanine.

Several substitutions at position 4 enhance the affinity compared to wildtype, these include Tyrosine, Tryphophan, 1 and 2-naphthylalanine (1/2 Nal) and 3,4 dichlorophenylalanine (3,4-DCPhe). The most potent substitution is 1-naphthylalanine, which enhances the affinity 7-fold.

Certain residues in loop 2 of 17-69-07 were examined for the purpose of enhancing stability of the molecule. These include residue 9, which contains the potential Tyr9 recognition point. Residue 11 is also attractive as it is permissive to substitution (Table 5) and vicinal to the Tyr9 recognition point.

TABLE 9

Summary of the tolerated amino acid substitutions

| Peptide code | Molecular Description | Kd (nM) |
|---|---|---|
| 17-69-07-N004 | Ac-(17-69-07) (wildtype) | 2.47 ± 0.25 |
| 17-69-07-N130 | Ac-(17-69-07) 4BrPhe9 | 2.45 ± 1.08 |
| 17-69-07-N182 | Ac-(17-69-07) 5FPhe9 | 13.1 |
| 17-69-07-N100 | Ac-(17-69-07) tBuGly11 | 1.56 ± 1.14 |

Of interest is 4-bromophenylalanine (4BrPhe), which alters the Tyr9 proteolytic recognition point, and tert-butylglycine (tBuGly), which slightly enhances the affinity and importantly, strongly protects the vicinal amino acid backbone from proteolytic hydrolysis by steric obstruction.

Multi-Site Substitutions to Achieve Global Proteolytic Protection of 17-69-07

The previous section disclosed multiple positions within the 17-69-07 sequence that permit inclusion of proteolytically stabilising and/or affinity enhancing amino acids.

In an effort to combine these modifications in a single molecule, a molecule was synthesised that incorporated a Tyr1→D-Ala1, Phe4→1Naphthylalanine4, Gly5→D-Ala5, Tyr9→4BrPhe9 and Ile11→tBuGly11 substitution. Remarkably, all modifications are tolerated in concert, and the potency is superior to that of the wild-type molecule (Tables 10 and 11).

TABLE 10

Results from a specific multi-substitution

| Peptide code | Molecular Description | Kd (nM) |
|---|---|---|
| 17-69-07-N004 | Ac-(17-69-07) (wildtype) | 2.47 ± 0.25 |
| 17-69-07-N252 | Ac-(17-69-07) D-Ala1 1Nal4 D-Ala5 4BrPhe9 tBuGly11 | 0.8 ± 0.39 |

In anticipation of attaching effector groups to such a bicyclic peptide during the further development of the molecule, versions were generated with an N-terminal sarcosine molecular spacer (10 consecutive Sar, denoted as Sar10) initiated with an N-terminal glycine and terminated with a C-terminal alanine. For the purpose of this experiment, the N-terminal Gly was capped with an acetyl group so as to remove the positive charge.

TABLE 11

Comparative data following G-Sar10-A addition

| Peptide code | Molecular Description | Kd (nM) |
|---|---|---|
| 17-69-07-N004 | Ac-(17-69-07) (wildtype) | 2.47 ± 0.25 |
| 17-69-07-N225 | Ac-G-Sar10-A-(17-69-07) | 0.95 ± 0.1 |
| 17-69-07-N239 | Ac-G-Sar10-A-(17-69-07) D-Ala1 1Nal4 D-Ala5 tBuGly11 | 0.94 ± 0.08 |

TABLE 11-continued

Comparative data following G-Sar10-A addition

| Peptide code | Molecular Description | Kd (nM) |
| --- | --- | --- |
| 17-69-07-N255 | Ac-G-Sar10-A-(17-69-07) D-Ala1 1Nal4 D-Ala5 4BrPhe9 tBuGly11 | 0.3 |

The data indicate that both molecular spacer (attached to the N-terminus as indicated) and the amino acid substitutions within the bicycle core sequence are well-tolerated, as potencies are retained or improved.

Table 12 shows the non-acetylated (non-)stabilised derivatives of the molecules shown in Table 11. Their stabilities were assessed quantitatively in mouse and human plasma in order to demonstrate an improvement compared to the non-stabilised 17-69-07-N219 (FIG. 1).

TABLE 12

Molecules selected for plasma stability assessment, associated potencies

| Peptide code | Molecular Description | Kd (nM) |
| --- | --- | --- |
| 17-69-07-N219 | G-Sar10-A-(17-69-07) (non-stabilised with spacer) | 0.82 ± 0.09 |
| 17-69-07-N244 | G-Sar10-A-(17-69-07) D-Ala1 1Nal4 D-Ala5 4BrPhe9 tBuGly11 | 0.45 ± 0.19 |
| 17-69-07-N231 | G-Sar10-A-(17-69-07) D-Ala1 1Nal4 D-Ala5 tBuGly11 | 1.07 ± 0.28 |
| 17-69-07-N241 | bAla-Sar10-A-(17-69-07) D-Ala1 1Nal4 D-Ala5 tBuGly11 | 1.21 ± 0.24 |

Figure 3:
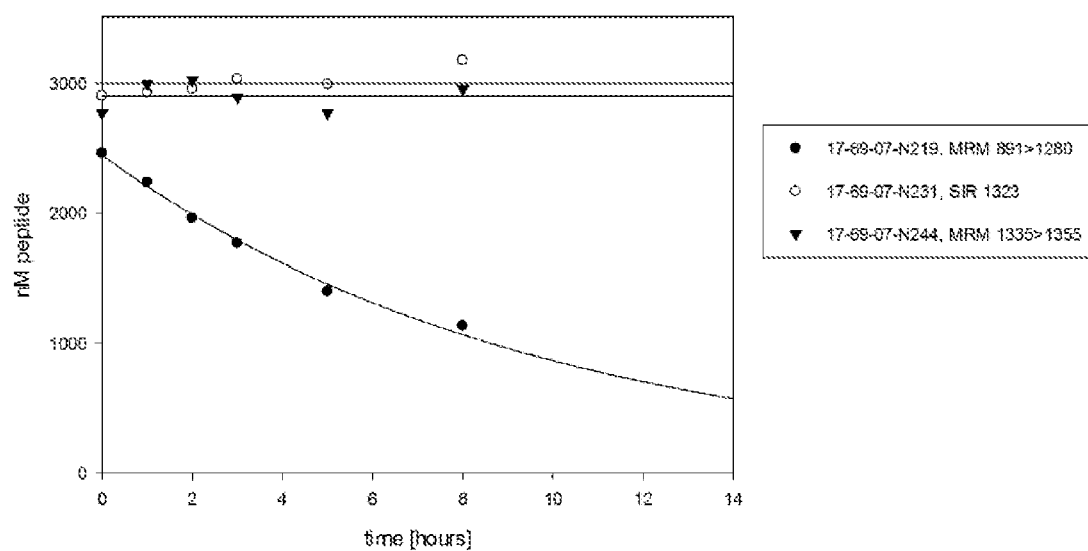
FIG. 3: (A) Mouse and (B) Human Plasma Stability of two stabilised 17-69-07 molecules (with 4-bromophenylalanine at position 9: 17-69-07-N244, without 4-bromophenylalanine at position 9: 17-69-07-N231) compared to the non-stabilised 17-69-07-N219. Several MRM transitions for a given analyte were monitored which correlated well between each other. For the purpose of this graph, only one transition is displayed.
Figure 3:
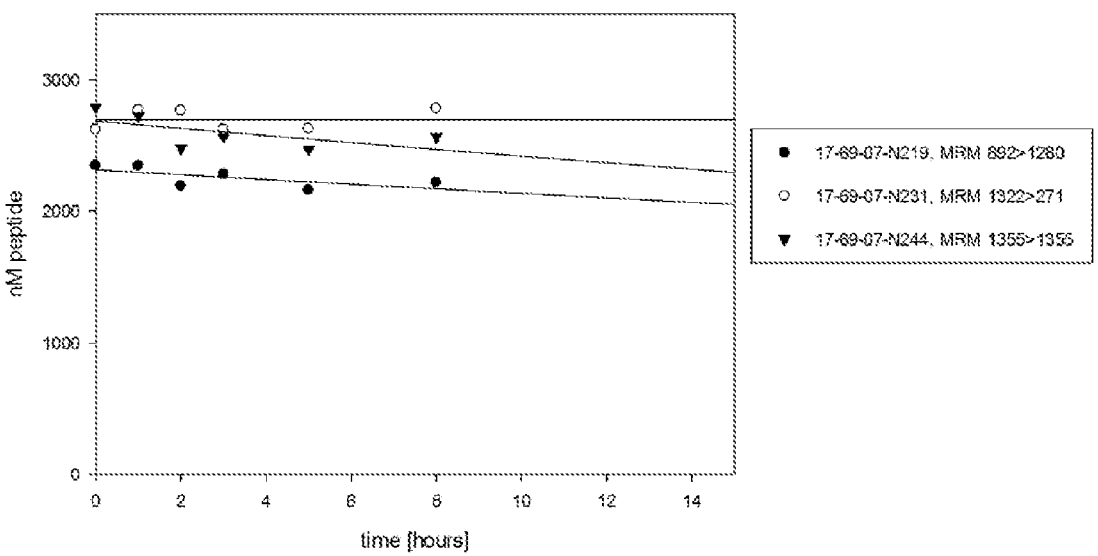

FIG. 3A shows the mouse plasma stability of the penta and tetra-substituted molecules 17-69-07-N244 and 17-69-07-N231, respectively, in comparison to the original non-stabilised wildtype molecule 17-69-07-N219. The half-life of the peptide in mouse plasma at 37° C. is >>20 hours, compared to 6 hours for the non-enhanced wildtype molecule.

FIG. 3B shows the human plasma stability of the penta and tetra-substituted molecules 17-69-07-N244 and 17-69-07-N231, respectively, in comparison to the original non-stabilised wildtype molecule 17-69-07-N219. The half-life of the peptide in mouse plasma at 37° C. is >>20 hours, compared to 6 hours for the non-enhanced wildtype molecule.

In summary, targeted substitutions at up to 5 positions in the 17-69-07 bicyclic core sequence (Tyr1→D-Ala1, Phe4→1Naphthylalanine4, Gly5→D-Ala5, Tyr9→4BrPhe9 and Ile11→tBuGly11) generated superior molecules with enhanced potency and significant improvement in plasma stability.

Selectivity of a Stabilised 17-69-07 Derivative (17-69-07-N241)

The stabilised, molecular spacer containing derivative 17-69-07-N241 was tested by FP competition for affinity to MT1-MMP hemopexin domain derived from other species. The data is summarised in Table 13:

TABLE 13

Species cross-reactivity of 17-69-07 and derivatives

| | Human/cyno (Kd, nM) | Dog (Kd, nM) | Mouse (Kd, nM) |
| --- | --- | --- | --- |
| 17-69-07-N219 | 0.82 | 0.9 | nd |
| 17-69-07-N241 | 1.21 | 1.4 | 0.63 |

Both non-stabilised and stabilised derivatives of 17-69-07 are fully cross reactive.

The N-terminally fluoresceinated derivative of 17-69-07-N241 (termed 17-69-07-N258, of the sequence: Fluorescein-(bAla)-Sar10-A-(17-69-07) D-Ala1 1Nal4 D-Ala5 tBu-Gly11) was tested against related human metalloproteinases. The data demonstrate that the 17-69-07 core sequence, and this stabilised variant, are uniquely selective for MT1-MMP (Table 14).

TABLE 14

Selectivity of 17-69-07 and derivatives to related metalloproteinases

| | V1T1-MMP (=MMP-14) (Kd, in nM) | MMP-1 (Kd, in nM) | MMP-2 (Kd, in nM) | MMP-15 (Kd, in nM) | MMP-16 (Kd, in nM) |
| --- | --- | --- | --- | --- | --- |
| 17-69-07-N258 | 2.2 | >1000 | >1000 | >1000 | >1000 |

Example 3: In Vivo Analysis of Proteolytically Stabilised Variants of 17-69-07 Conjugated to a Chelator Peptides linked to metal chelators have multiple applications in diagnostics and therapeutics. Certain imaging or therapeutic radioisotopes can be "loaded" onto the chelator while the peptide carries said isotopes to the target. In this manner, tumour specific antigens can be visualised using, for example, PET and SPECT scanners. For targeted radiotherapy, therapeutic radionuclides (such as $^{90}Y$ and $^{177}Lu$) are loaded onto the chelator-peptide and selectively carried to the tumour by binding the tumour-associated antigen. There they exert their anti-tumour activity by the high energy radiation they emit.

Synthesis of Chelator-Linked 17-69-07 Bicyclic Peptides

Five derivatives were synthesised where the metal chelator DOTA (1,4,7,10-tetraazacyclododecane-1,4,7,10-tetraacetic acid) was linked to the N-terminal Alanine of the 17-69-07 bicyclic peptide.

TABLE 15

Summary of the molecules and structure

| Peptide code | Molecular Description | Kd (nM) |
| --- | --- | --- |
| 17-69-07-N144 | DOTA-A-(17-69-07) | 0.5 |
| 17-69-07-N147 | DOTA[Lu]-A-(17-69-07) | 0.95 ± 0.5 |
| 17-69-07-N248 | DOTA-A-(17-69-07) D-Ala1 1Nal4 D-Ala5 4BrPhe9 tBuGly11 | 0.5 |
| 17-69-07-N246 | DOTA-A-(17-69-07) All D Amino Acids | >5000 |

17-69-07-N144 is the wildtype sequence of 17-69-07 where DOTA is directly linked to an N-terminal Alanine that serves as a one amino acid spacer. This molecule retains full potency to MT1-MMP. To demonstrate that potency is retained when loaded with a therapeutic/imaging radionuclide, the chelator was loaded with the natural (cold) $^{175}$Lutetium as a safe substitute. Potency was retained.

The fully stabilised variant, 17-69-07-N248, also retained potency in the context of the DOTA conjugate.

A control molecule was prepared, 17-69-07-N246, which is the full D-amino acid equivalent of 17-69-07-N144. This molecule is completely resistant to proteolytic degradation as amide bonds adjacent to D amino acids are protected from proteases, and lacks any activity toward MT1-MMP. Importantly, this peptide retains the exact same sequence and chemical composition.

Biodistribution of $^{177}$Lu-Loaded 17-69-07-N144 in HT1080 Xenograft Mice

HT-1080 cells (which are known to abundantly express MT1-MMP) were subcutaneously inoculated into the right trunk of male 6-week-old BALB/c nu/nu mice. The tumours were allowed to grow for approx. 1 week.

150 pmole of 17-69-07-N144 peptide was loaded with 1 MBq of the γ- and β-emitter $^{177}$Lu using standard complexation techniques. Per tumour-bearing mouse, 150 pmole of the loaded 17-69-07-N144 was then injected (the equivalent of 17 µg/kg). 3 animals were euthanized per time point, various organs and tumour excised and weighed, and followed by determination of the gamma-radiation count per gram of tumour/organ tissue. The resulting plot gives a quantitative indication of the localisation of the peptide in the in vivo mouse. In particular, selective accumulation in the HT1080 tumour indicates MT1-MMP binding in vivo.

Figure 4:
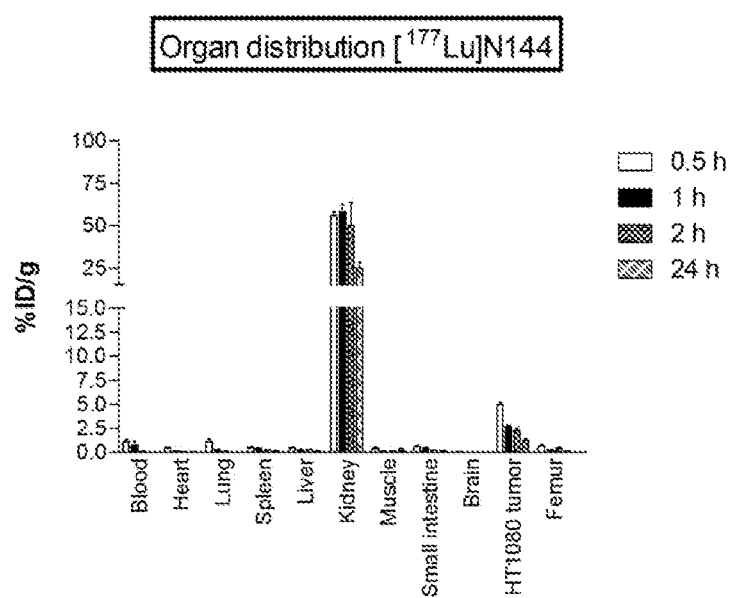
FIG. 4: Biodistribution of $^{177}$Lu 17-69-07-N144 in HT-1080 xenograft mice.

FIG. 4 summarises the biodistribution data. Remarkably, the bicyclic peptide is specific for the tumour and appears to persist up to 24 hours, despite an estimated half-life in the circulation of 14 min. This likely indicates uptake into the tumour cells. Significant localisation is visible at the kidneys, and it is likely that this is due to kidney amino acid transporters transiently binding the peptide. All other organs do not show significant uptake of the molecule. Of note, the mouse hemopexin domain shares full homology with the human counterpart, indicating that if mouse PEX were expressed elsewhere, corresponding signals would be observed.

Figure 5:
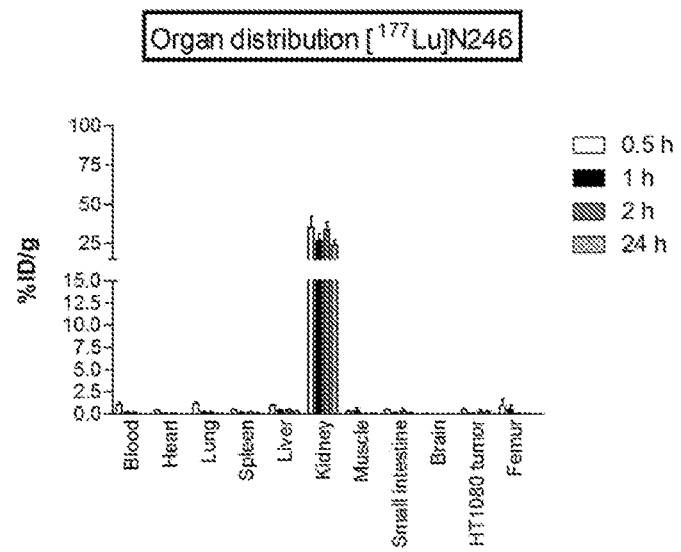
FIG. 5: Biodistribution of $^{177}$Lu 17-69-07-N246 in HT-1080 xenograft mice.

To assess whether tumour uptake in the xenograft model is selective and due to PEX binding, an additional study was performed using the peptide 17-69-07-N246, which is the D-amino acid counter-part of 17-69-07-N144 (FIG. 5).

Comparing the biodistribution pattern to the one obtained with the active bicyclic peptide 17-69-07-N144, it is clear that the MT1-MMP non-binding 17-69-07-N246 bicyclic peptide does not target the tumour, confirming that the tumour signal of 17-69-07-N144 is driven by MT1-MMP target binding in vivo.

Figure 6:
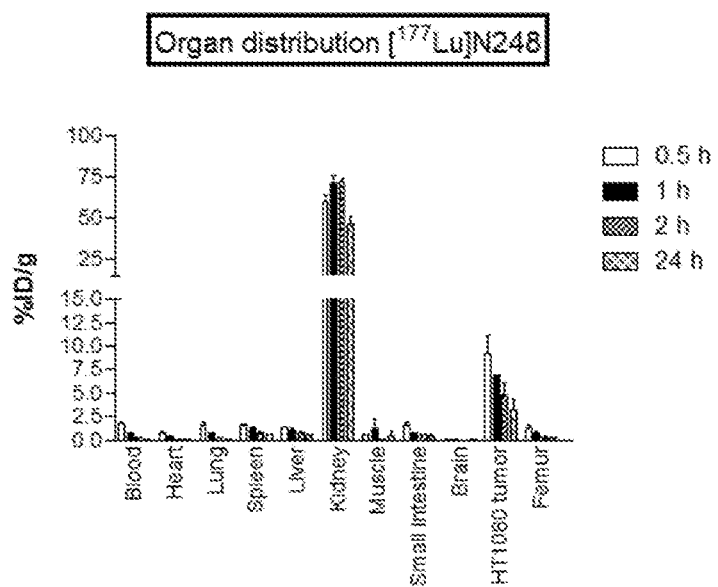
FIG. 6: Biodistribution of $^{177}$Lu 17-69-07-N248 in HT-1080 xenograft mice.

Finally, to assess the effect of proteolytic stabilisation of the 17-69-07 sequence on biodistribution, bicyclic peptide 17-69-07-N248 (DOTA-A-(17-69-07) D-Ala1 1Nal4 D-Ala5 4BrPhe9 tBuGly11) was employed in an identical biodistribution study (FIG. 6).

Strikingly, the enhanced proteolytic stability of the peptide leads to an overall doubling of the tumour uptake at any given time point compared to 17-69-07-N144, exemplifying the superior properties of the molecule compared to the original, non-stabilised 17-69-07 sequence.

It is anticipated that this effect could result in an advantageous therapeutic index, both for radionuclide targeted therapy using the conjugates described in this example and in the context of toxin-conjugated bicyclic peptides (Example 4).

Example 4: Conjugation of Non-Stabilised Bicyclic Peptides with Cytotoxic Agents For targeted cancer therapy, highly potent cytotoxic drugs are attached through a cleavable linker to a targeting entity (here, a bicyclic peptide), which binds to tumour-associated cell surface-expressed proteins. The overexpressed tumour associated cell surface protein target is selected for its ability to internalise into the interior of the cell. Upon binding of the cytotoxic agent-conjugated targeting entity to the tumour-associated cell surface protein, the entire molecular complex internalises to the inside of the cell. Following the transition from the systemic circulation into the distinct intracellular environment, the cytotoxic drug is cleaved from the targeting entity by intracellular conditions, and the cleaved drug then exerts its anti-tumour activity by inducing targeted cell-death through cell-cycle arrest followed by apoptosis.

Bicyclic peptide 17-69-07-N219 (see Examples 2 and 3) is composed of the wildtype bicyclic core sequence linked on the N-terminal side to a Gly-Sar10-Ala molecular spacer (G-Sar10-A-(17-69-07), where the full sequence description is G-Sar10-A-CYNEFGCEDFYDIC; SEQ ID NO: 20). This derivative of (17-69-07) retains full potency (Table 12) to MT1-MMP at a Kd of 0.8 nM. The free, unique amino group at N-terminal side of the molecular spacer is ideally placed for conjugation with effector groups such as highly potent cytotoxic substances. The long intramolecular distance imparted by the Sar10 linker between the conjugation site on the N-terminal Gly and the bicycle core sequence is employed so as to guarantee full retention of target binding potency following conjugation with effector groups of significant molecular size. Shorter molecular spacers may be selected at will so long as the potency of the bicycle core sequence to the target protein is retained.

To generate proof of concept data with a Bicyclic peptide Drug Conjugate (termed BDC) targeting MT1-MMP, two conjugates of 17-69-07-N219 were prepared, which either employed the microtubule polymerisation-inhibiting toxins DM1 (a maytansine, also known as N2'-Deacetyl-N2'-(3-Mercapto-1-Oxopropyl)-Maytansine) or MMAE (Monomethylauristatin E, also known as (S)-N-((3R,4S,5S)-1-((S)-2-((1R,2R)-3-(((1S,2R)-1-hydroxy-1-phenylpropan-2-yl) amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide).

The MMAE conjugate is termed BT17BDC-1 and is separated from the 17-69-07-N219 precursor by a Valine-Citrulline (Val-Cit) linker including the self-immolating para-aminobenzyl-carbonyl group (PABC). The Val-Cit linker is selectively cleaved (hydrolysed) by the Cathepsin B-rich environment encountered in the intracellular lysosomes, and following hydrolysis, PABC immolates to release MMAE as the active toxic species. The Val-Cit-PABC linker is stable in the circulation, and thus releases the toxin only upon cell internalisation.

The structure of the conjugate, and the synthetic scheme for the preparation of BT17BDC-1, is shown in Scheme I:

Scheme I

Structure of BT17BDC-1

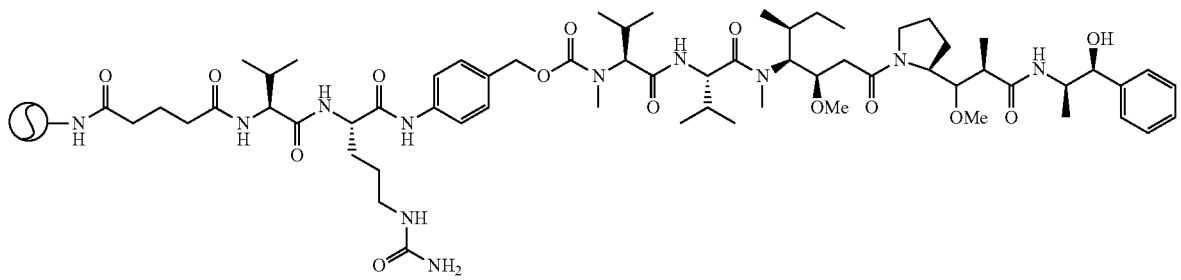

17-69-07-N219
BT17BDC-1

Reaction Scheme:

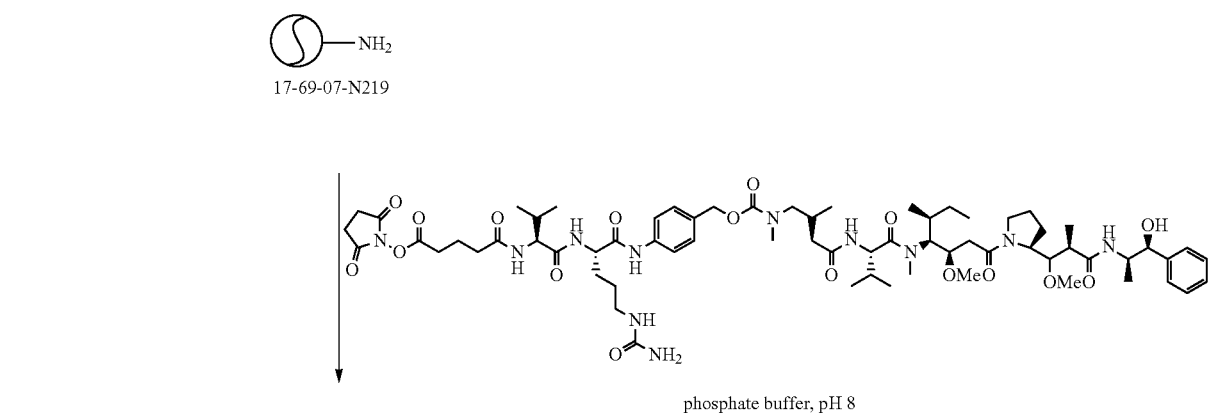

phosphate buffer, pH 8

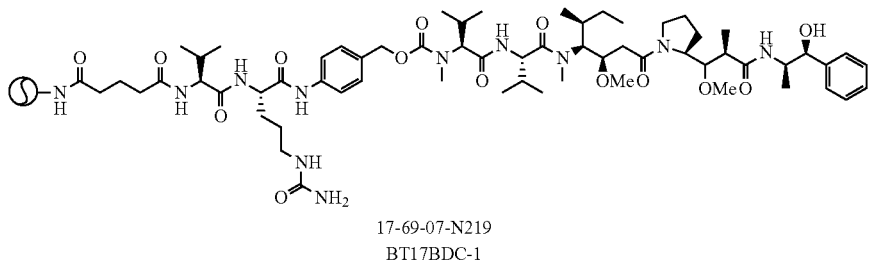

17-69-07-N219
BT17BDC-1

Synthetic strategy for preparation of BDC17BDC-1: The fully purified, TMB cyclised 17-69-07-N219 bicycle precursor is reacted with the succinimide ester of glutaryl-Valine-citrulline-p-aminobenzylcarbonyl-MMAE (commonly abbreviated as vc-MMAE or Val-Cit-PABC-MMAE), yielding the conjugate BDC17BDC-1.

The DM1 conjugate of 17-69-07-N219 is termed BT17BDC-9 and is separated from the 17-69-07-N219 precursor by a disulphide bond, which can be cleaved by the reducing environment encountered in the intracellular milieu. The reduction is believed to take place through intracellular glutathione, which is present at ~10 mM concentrations inside the cell. By contrast, the concentration of glutathione and free reducing agents in the blood circulation is much lower (<10 μM); thus the toxin is released predominantly in the intracellular environment, where it can unfold its cell killing activity.

The structure of the conjugate, and the synthetic scheme for the preparation of BT17BDC-9, is shown in Scheme II:

Scheme II
Structure of BT17BDC-9
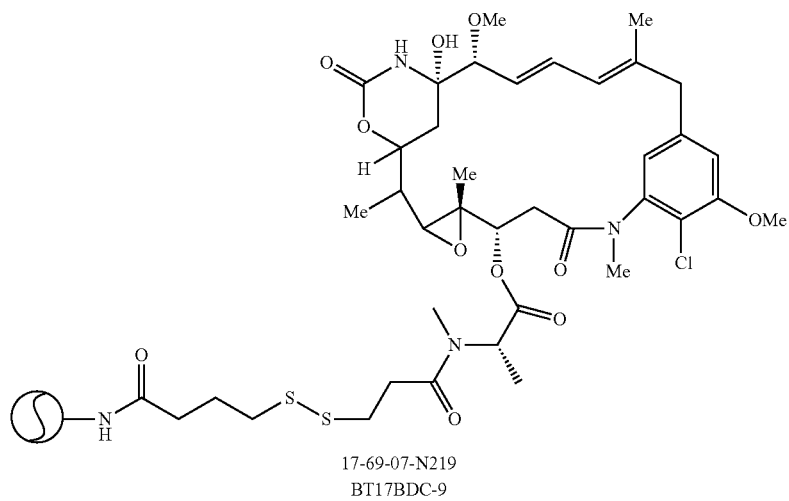
17-69-07-N219
BT17BDC-9
Reaction Scheme:
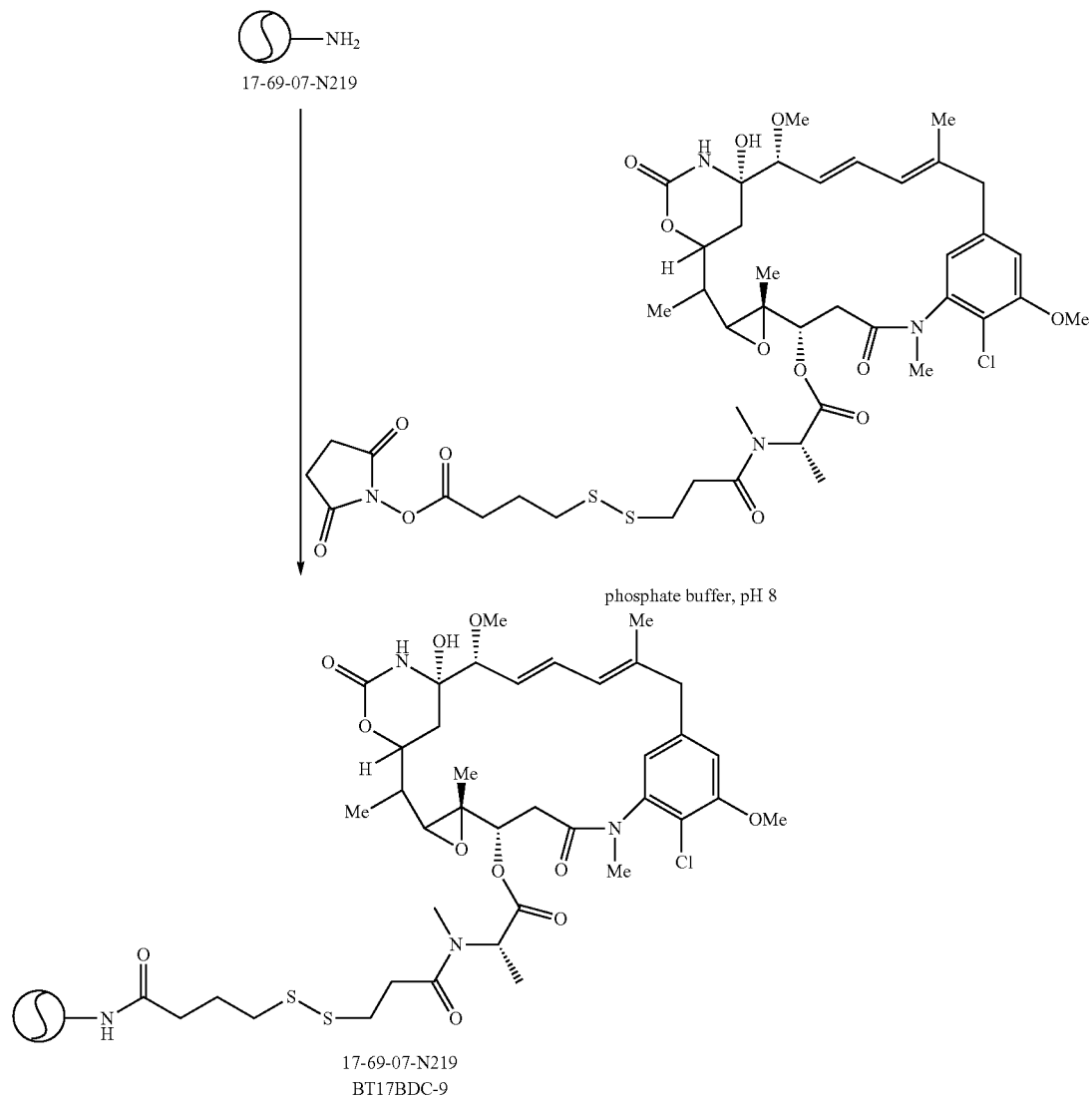
17-69-07-N219
BT17BDC-9

Synthetic strategy for preparation of BDC17BDC-9: The fully purified, TMB cyclised 17-69-07-N219 bicycle precursor containing the free, N-terminal amine, is reacted with the succinimide ester of disulphide-DM1 (structure as shown), yielding the conjugate BDC17BDC-9.

The release of the toxins in BDC17BDC-1 and BDC17BDC-9 is therefore mechanistically distinct, i.e. the former through intracellular proteolytic conditions, and the latter by intracellular reducing conditions.

The two BDCs were employed in in vitro cytotoxicity studies and showed low nanomolar/picomolar potency on cell cultures such as HT1080 (data not shown).

Figure 7:
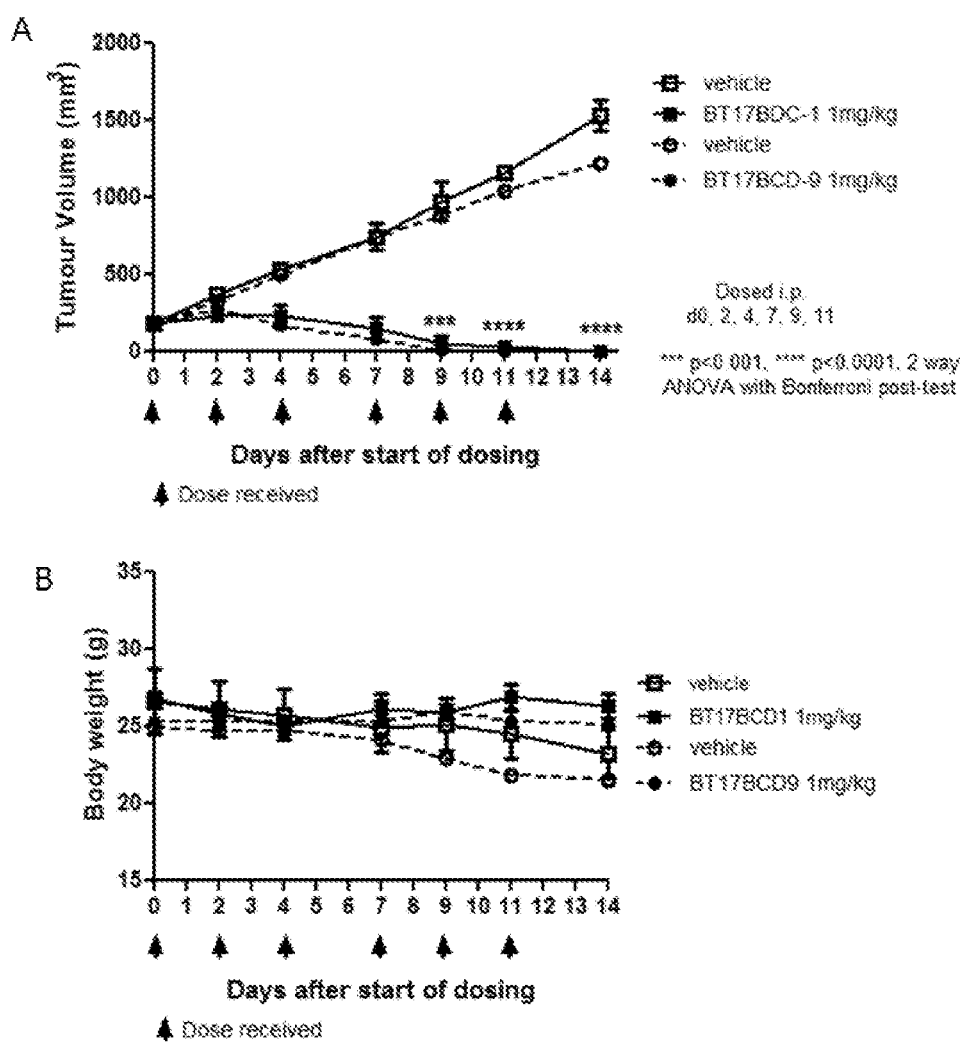
FIG. 7: (A): Plot of mean tumour volume versus time for BT17BDC-1 and 9. Doses were administered on day 0, 2, 4, 7, 9, and 11. (B): Body weight during treatment, which is indicative of drug-associated toxicology and overall animal health.

In an in vivo mouse xenograft model (harbouring HT1080 tumours), both BDCs caused significant reduction in tumour volume after 9 days post injection compared to vehicle control. The dosage regime is indicated in FIG. 7 (arrows). Tumours were completely cleared by day 14 for both BDCs, as judged by palpation (FIG. 7). Notably, the weight of the animals for both BDC17BDC-1 and BDC17BDC-9 were largely stable, indicating a therapeutic window that could be sufficient for therapeutic purposes.

Example 5: Conjugation of Proteolytically Stabilised Bicyclic Peptides with Cytotoxic Agents The bicyclic core sequence 17-69-07 containing the modifications of D-alanine at position 1, 1-naphthylalanine at position 4, D-alanine at position 5, and α-tert-butylglycine at position 11 with or without 4-bromophenylalanine at position 9, had enhanced proteolytic stability in ex vivo plasma and in vivo (Examples 2, 3).

In the context of bicycle drug conjugates, it is likely that a more stable bicycle core sequence could lead to greater tumour exposure due to reduced systemic clearance and greater stability in the proteolytically aggressive tumour microenvironment. Both can result in increased MT1-MMP driven uptake of BDC to inside the cell, leading to an increase in therapeutic efficacy.

The stabilised bicyclic peptide 17-69-07-N241 was designed with an overall similar molecular layout to the non-stabilised 17-69-07-N219 (described in Examples 3 and 4). It has the following sequence:

```
                                            (SEQ ID NO: 5)
(B-Ala)-Sar10-AC(D-Ala)NE(1Nal)(D-Ala)CEDFYD (tBuGly)C
``` which is cyclised with TBMB as before.

The N-terminal beta-alanine was selected rather than the previously employed glycine as in 17-69-07-N219 so as to minimise diketopiperazine side product formation during the coupling with N-hydroxysuccinimide (NHS) esters (Purdie et al (1973), J. Chem. Soc., Perkin Trans. 2, 1845), specifically in this example with NHS esters of cytotoxic agents (Scheme I, II).

The sarcosine decamer spacer is retained as in 17-69-07-N219 so as to ensure full retention of binding of the bicycle peptide to the hemopexin domain of MT1-MMP.

The maytansine toxin class was selected for conjugation to 17-69-07-N241 based on the efficacy and tolerability in the mouse xenograft model described in Example 4, and the disulphide cleavable linker was again selected.

Four BDCs were prepared (referred to hereinbefore as BT17BDC-17, BT17BDC-18, BT17BDC-19 and BT17BDC-20), whereby both toxin and 17-69-07-N241 were invariant, while the disulphide bond susceptibility to reduction/cleavage was altered by modulating the degree of hindrance adjacent to the sulphur atoms.

The synthetic route to the conjugates is as described in Scheme II, wherein 17-69-07-N219 is replaced with 17-69-07-N241.

For BT17BDC-18, an additional route to synthesis involved generation of a pyridyl-disulphide bicycle precursor (termed 17-69-07-N277), which is reacted with DM1 to form the full conjugate. The synthetic route is described in Scheme III.

Scheme III

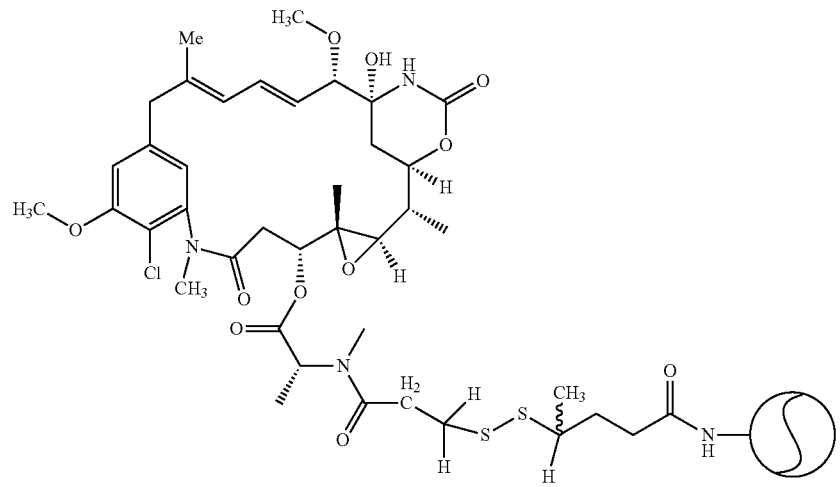

Structure of BT17BDC-18
17-69-07-N241

-continued
Reaction Scheme

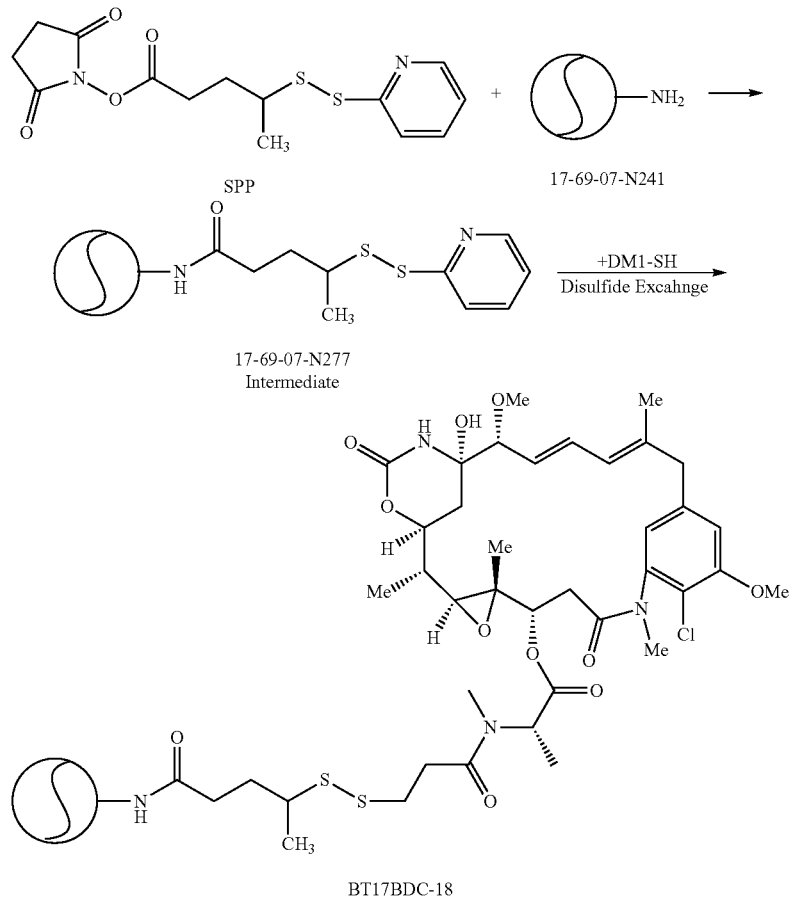

BT17BDC-18

Synthetic strategy for preparation of BDC17BDC-18: The fully purified, TMB cyclised 17-69-07-N241 bicycle precursor containing the free, N-terminal amine, is reacted with the SPP (N-succinimidyl 4-(2-pyridyldithio)pentanoate)), yielding the Intermediate 17-69-07-N277. This is then reacted with DM1 as the free thiol, yielding the desired conjugate BT17BDC-18.

In Vitro Characterisation of BT17BDC-17, BT17BDC-18, BT17BDC-19 and BT17BDC-20

The four BDCs were assessed for several in vitro parameters such as retention of potency to the human MT1-MMP hemopexin domain, stability in ex vivo mouse, rat and human plasma, and stability to reducing agents such as dithiothreitol.

The data is summarised in Table 16 below:

TABLE 16

In vitro properties of BT17BDC-17, BT17BDC-18, BT17BDC-19 and BT17BDC-20

| Bicycle Drug Conjugate | Kd (nM) (Hemopexin domain)[a] | $t_{1/2}$ (hrs) (human plasma)[b] | $t_{1/2}$ (hrs) (mouse plasma)[b] | $t_{1/2}$ (hrs) (rat plasma)[b] | Relative Stability to DTT (ADC)[c] | Relative Stability to DTT (BDC)[d] |
|---|---|---|---|---|---|---|
| 17-69-07-N219 | 0.82 ± 0.09 (n = 3)[e] | 30.3 ± 4.7 (n = 1) | 3.9 ± 0.3 (n = 1) | 3.7 ± 0 (n = 1) | n/a | n/a |
| 17-69-07-N241 | 1.4 ± 0.3 (n = 10)[e] | >36 (n = 2) | >36 (n = 2) | >36 (n = 1) | n/a | n/a |
| BT17BDC-17 | 0.7 (n = 1)[e] | 4.2 ± 0 (n = 2) | 5.5 ± 0.7 (n = 1) | 1.2 ± 0.1 (n = 1) | 1 | 1 |
| BT17BDC-18 | 0.99 ± 0.17 (n = 6)[e] | 12.7 ± 2.2 (n = 2) | 14.3 ± 1 (n = 2) | 4.3 ± 0.6 (n = 2) | 7 | 5 |

TABLE 16-continued

In vitro properties of BT17BDC-17, BT17BDC-18, BT17BDC-19 and BT17BDC-20

| Bicycle Drug Conjugate | Kd (nM) (Hemopexin domain)[a] | $t_{1/2}$ (hrs) (human plasma)[b] | $t_{1/2}$ (hrs) (mouse plasma)[b] | $t_{1/2}$ (hrs) (rat plasma)[b] | Relative Stability to DTT (ADC)[c] | Relative Stability to DTT (BDC)[d] |
|---|---|---|---|---|---|---|
| BT17BDC-19 | 0.5 (n = 1)[e] | 23.5 ± 4.1 (n = 2) | >36 (n = 1) | >36 (n = 1) | 14 | 30 |
| BT17BDC-20 | 2.95 ± 1.3 (n = 4)[f] | 32 ± 1 (n = 1) | >36 (n = 1) | 34 ± 4 (n = 1) | 170 | 93 | where n/a: not applicable, and where n = numbers of repeats
[a] determined by fluorescence polarisation competition experiments using 17-69-07-N040 as a tracer
[b] determined using quantitative LC-MS. Incubation time up to 24 hrs in plasma, containing 4 µM BDC.
[c] from Kellogg et al (2011) Bioconjugate Chemistry, 22, 717. Note these values relate to antibody drug conjugates containing the disulphide linker described in the text
[d] determined by quantitative LC-MS. Note these values relate to Bicycle Drug Conjugates containing the disulphide linker described in the text. Methods were adapted from Kellogg et al (2011) Bioconjugate Chemistry, 22, 717.
[e] Use of 17-69-07-N004 as tracer in FP competition
[f] Use of 17-69-07-N040 as tracer in FP competition
All molecular constructs retain their affinity to the hemopexin target (second column).

The data indicates that plasma stability is governed by the nature of the disulphide bond (as modulated by susceptibility to reduction), and not the nature of the bicyclic peptide, since all BDCs contain the same bicyclic peptide (17-69-07-N241) which is stable in the plasma from the three species tested.

Furthermore, BT17BDC-18, BT17BDC-19 and BT17BDC-20 show stabilities in human plasma adequate for therapeutic use, since the anticipated renal filtration driven clearance of the peptides of this molecular size in man has an estimated half-life of 2 to 4 hours, which is several-fold faster than the degradation half-life of the BDCs in human plasma (>14 hrs BT17BDC-18/19/20, see Table 16). Thus, the bulk of the BDC is expected to clear renally, with only a fraction being degraded in the circulation, making these BDCs potentially suitable for therapeutic purposes.

In Vivo Efficacy of BT17BDC-17, BT17BDC-18, BT17BDC-19 and BT17BDC-20

All BDCs containing the stabilised bicycle core sequence were tested for their efficacies in in vivo mouse xenograft models, using the human lung squamous cell carcinoma line EBC-1.

Figure 9:
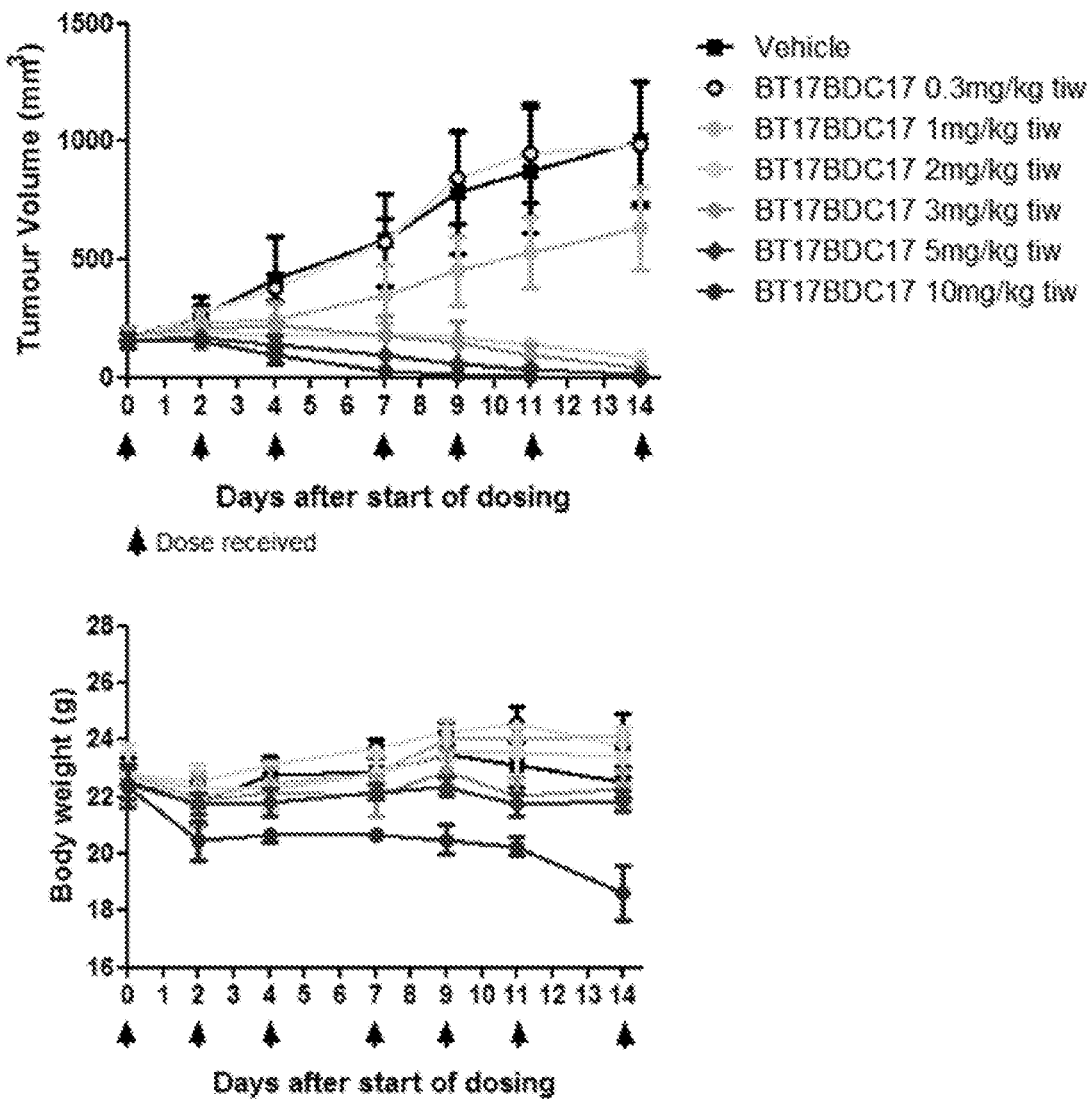
FIG. 9: Top: Plot of mean tumour volume versus time for BT17BDC-17 in EBC-1 xenograft mice. Doses were administered on day 0, 2, 4, 7, 9, 11 and 14. Bottom: Body weight during treatment, which is indicative of drug-associated toxicology and overall animal health.
Figure 10:
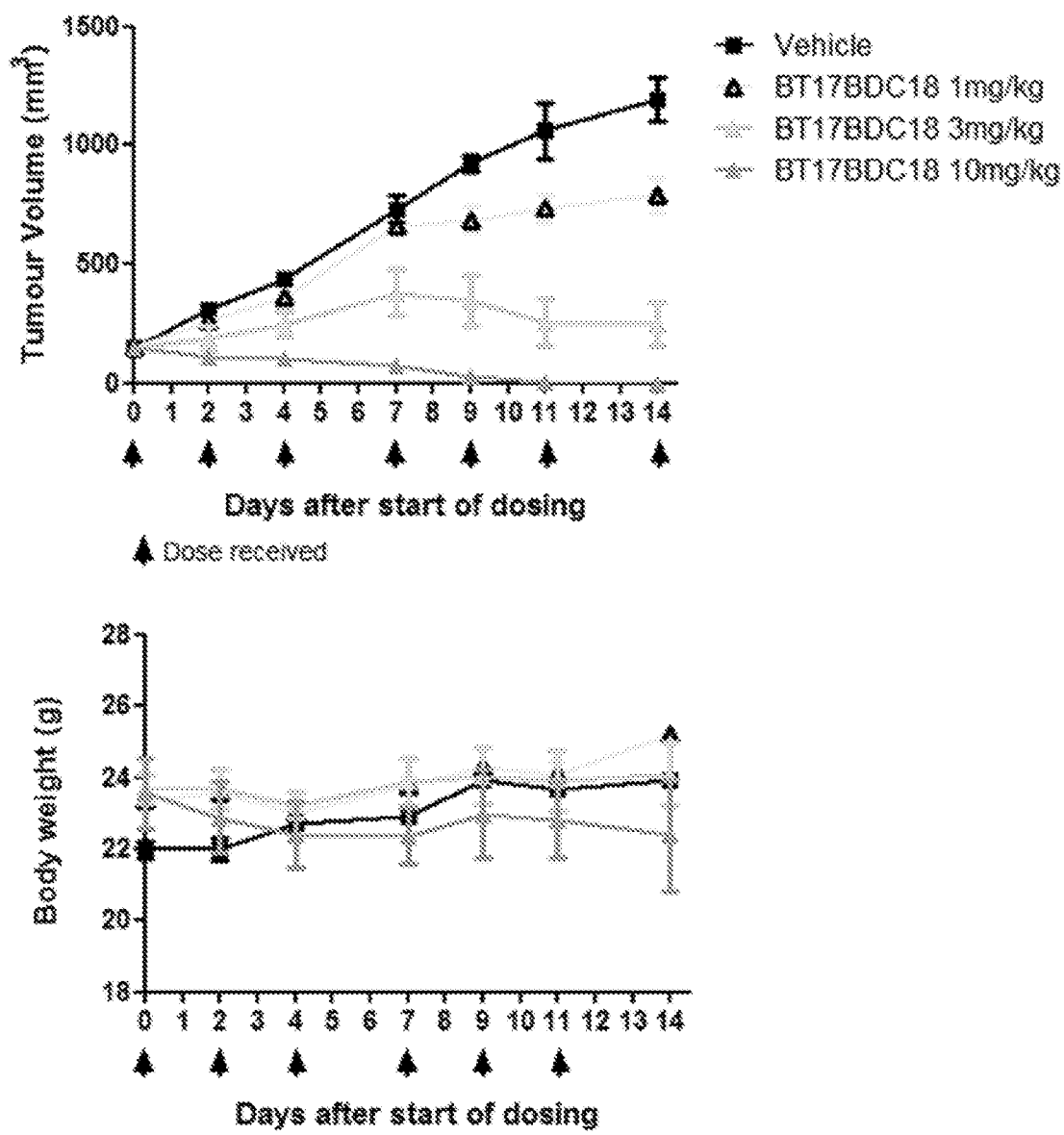
FIG. 10: Top: Plot of mean tumour volume versus time for BT17BDC-18 in EBC-1 xenograft mice. Doses were administered on day 0, 2, 4, 7, 9, 11 and 14. Bottom: Body weight during treatment, which is indicative of drug-associated toxicology and overall animal health.
Figure 11:
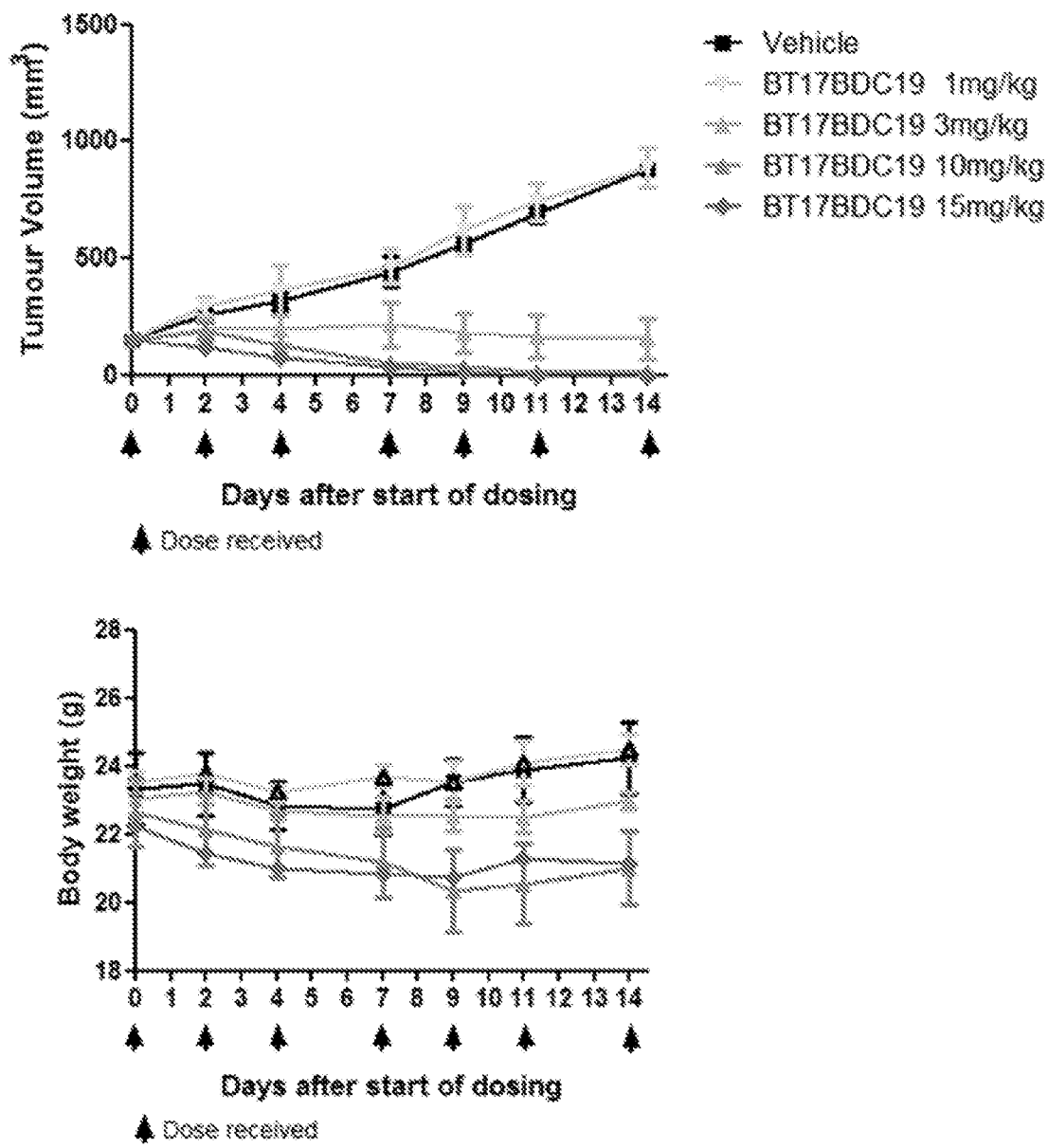
FIG. 11: Top: Plot of mean tumour volume versus time for BT17BDC-19 in EBC-1 xenograft mice. Doses were administered on day 0, 2, 4, 7, 9, 11 and 14. Bottom: Body weight during treatment, which is indicative of drug-associated toxicology and overall animal health.
Figure 12:
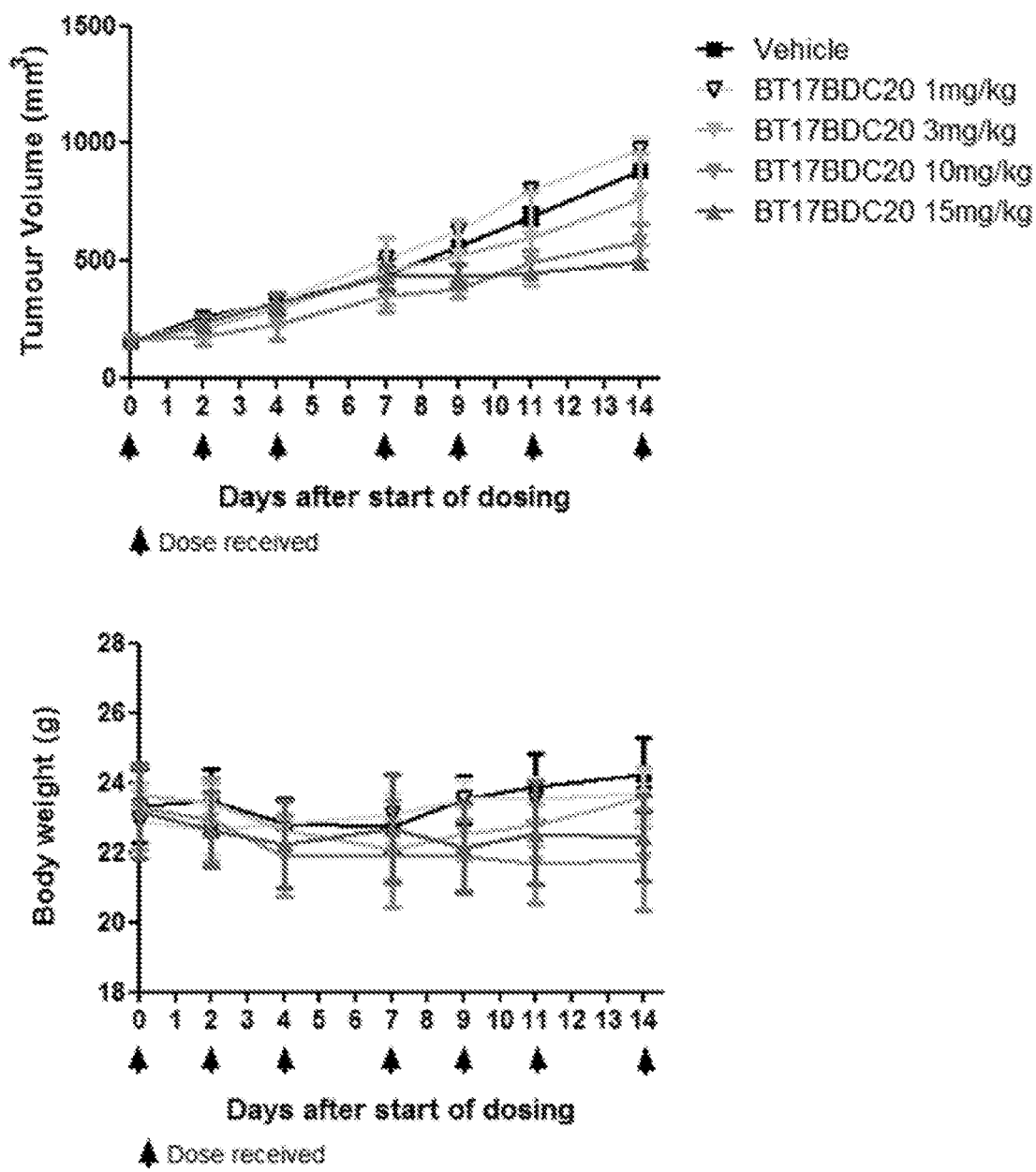
FIG. 12: Top: Plot of mean tumour volume versus time for BT17BDC-20 in EBC-1 xenograft mice. Doses were administered on day 0, 2, 4, 7, 9, 11 and 14. Bottom: Body weight during treatment, which is indicative of drug-associated toxicology and overall animal health.

BT17BDC-17, BT17BDC-18 and BT17BDC-19 were efficacious and cleared tumours in 9 days (FIGS. 9, 10 and 11). BT17BDC-17 showed good efficacy, but some weight reduction at high doses. BT17BDC-20 was, whilst tolerated based on constant weight, not efficacious and only caused a marginal reduction in tumour sizes (FIG. 12).

Figure 13:
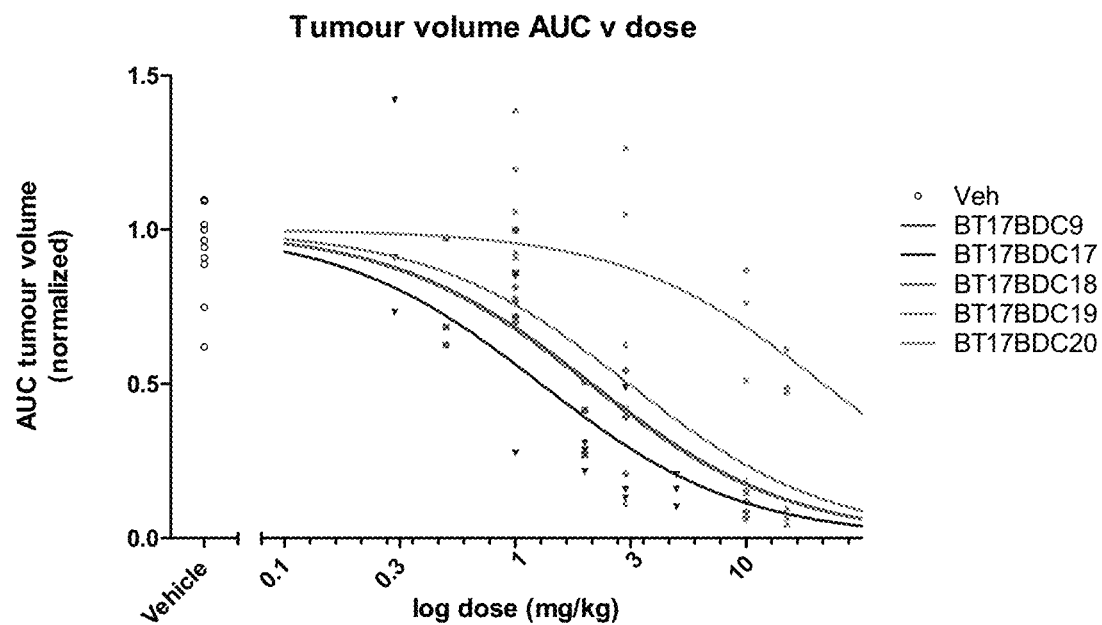
FIG. 13: Plot of the area under the curve (AUC) of tumour volume over time associated with a particular BDC against the corresponding dose group. Curve fits are performed using all available data points normalised for tumour volume at time zero, using standard IC 50 equations.

The area under the curve (AUC) of tumour volume over time and BDC was taken and plotted against the corresponding dose group (FIG. 13). From this, the effective dose to achieve 50% tumour AUC reduction (ED50) can be determined, which is summarised in Table 17.

TABLE 17

Effective dose to achieve 50% tumour AUC reduction for BT17BDC-9, BT17BDC-17, BT17BDC-18, BT17BDC-19 and BT17BDC-20

| BDC | BT17BDC-9 | BT17BDC-17 | BT17BDC-18 | BT17BDC-19 | BT17BDC-20 |
|---|---|---|---|---|---|
| ED50[a] | 2.1 ± 1.1[b] | 1.3 ± 0.6[b] | 2.1 ± 0.8[b] | 3.1 ± 1.6[b] | 22 ± 13[b] |

[a] ED50 ± 95% confidence limit
[b] units in mg/kg, in mouse bearing EBC-1 tumours Thus, BT17BDC-9, BT17BDC-17, BT17BDC-18 and BT17BDC-19 are suitable molecules for use in targeted cancer therapy based on efficacy, and BT17BDC-17, BT17BDC-18 and BT17BDC-19 are well tolerated at efficacious doses.

The invention claimed is:

1. A peptide ligand specific for MT1-MMP (membrane type 1 metalloprotease), or a pharmaceutically acceptable salt thereof, comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises the amino acid sequence:

(I)                                                         (SEQ ID NO: 1)
$-C_i-X_1-U/O_2-X_3-X_4-G_5-C_{ii}-E_6-D_7-F_8-Y_9-X_{10}-X_{11}-C_{iii}-$ wherein:

$C_i$, $C_{ii}$ and $C_{iii}$ represent first, second and third cysteine residues, respectively;

each of $X_1$, $X_3$, $X_4$, $X_{10}$ and $X_{11}$ represents any natural amino acid residue;

$U/O_2$ represents that position 2 of the loop sequence between $C_i$ and $C_{ii}$ is U or O;

U represents a polar, uncharged amino acid residue selected from the group consisting of N, C, Q, M, S and T; and O represents a non-polar aliphatic amino acid residue selected from the group consisting of G, A, I, L, P and V.

2. The peptide ligand according to claim 1, or a pharmaceutically acceptable salt thereof, wherein $X_1$ is selected from the group consisting of Y, M, F and V.

3. The peptide ligand according to claim 1, or a pharmaceutically acceptable salt thereof, wherein $U/O_2$ represents N or G.

4. The peptide ligand according to claim 1, or a pharmaceutically acceptable salt thereof, wherein $X_3$ is U or Z, wherein U is selected from the group consisting of N, C, Q, M, S and T, and Z is selected from the group consisting of D and E; or wherein U is Q and Z is E.

5. The peptide ligand according to claim 1, or a pharmaceutically acceptable salt thereof, wherein $X_4$ is selected from the group consisting of F, W and Y.

6. The peptide ligand according to claim 1, or a pharmaceutically acceptable salt thereof, wherein $X_{10}$ is selected from the group consisting of D and E; and $X_{11}$ is selected from the group consisting of G, A, I, L, P and V.

7. The peptide ligand according to claim 1, or a pharmaceutically acceptable salt thereof, wherein the amino acid sequence SEQ ID NO: 1 is selected from the group consisting of:

(SEQ ID NO: 6)
$-C_i-Y/M/F/V-U/O-U/Z-J-G-C_{ii}-E-D-F-Y-Z-O-C_{iii}-,$ (SEQ ID NO: 7)
$-C_i-Y/M/F/V-N/G-E/Q-F-G-C_{ii}-E-D-F-Y-D-I-C_{iii}-,$

```
                                                  (SEQ ID NO: 8)
-C_i-Y/M/F-N/G-E/Q-F-G-C_{ii}-E-D-F-Y-D-I-C_{iii}-, (SEQ ID NO: 9)
-C_i-Y/M-N-E/Q-F-G-C_{ii}-E-D-F-Y-D-I-C_{iii}-, and (SEQ ID NO: 2)
-C_i-Y-N-E-F-G-C_{ii}-E-D-F-Y-D-I-C_{iii}-.
```

8. The peptide ligand according to claim 1, or a pharmaceutically acceptable salt thereof, wherein the amino acid sequence SEQ ID NO: 1 is selected from the group consisting of:

```
                                                  (SEQ ID NO: 2)
-C_i-Y-N-E-F-G-C_{ii}-E-D-F-Y-D-I-C_{iii}-;

(SEQ ID NO: 10)
-C_i-M-N-Q-F-G-C_{ii}-E-D-F-Y-D-I-C_{iii}-;

(SEQ ID NO: 11)
-C_i-F-G-E-F-G-C_{ii}-E-D-F-Y-D-I-C_{iii}-;

(SEQ ID NO: 12)
-C_i-V-N-E-F-G-C_{ii}-E-D-F-Y-D-I-C_{iii}-;

(SEQ ID NO: 13)
-C_i-F-N-E-F-G-C_{ii}-E-D-F-Y-D-I-C_{iii}-;

(SEQ ID NO: 14)
-C_i-Y-N-E-Y-G-C_{ii}-E-D-F-Y-D-I-C_{iii}-;
and (SEQ ID NO: 15)
-C_i-Y-N-E-W-G-C_{ii}-E-D-F-Y-D-I-C_{iii}-.
```

9. The peptide ligand according to claim 1, or a pharmaceutically acceptable salt thereof, which is a free acid or a sodium, potassium, calcium, or ammonium salt.

10. The peptide ligand according to claim 1, or a pharmaceutically acceptable salt thereof, which is a high affinity binder of the human, mouse and dog MT1-MMP hemopexin domain, wherein the peptide ligand does not cross-react with MMP-1, MMP-2, MMP-15 and MMP-16.

11. A drug conjugate BT17BDC-18, which is of formula (IV):

(IV)

[Chemical structure showing Toxin connected via linker with $[CH_2]_n$, $R_1$, $R_2$, S-S bridge, $R_3$, $R_4$, $[CH_2]_m$, to Bicycle]

wherein:
  Toxin is the cytotoxic agent DM1;
  Bicycle represents a peptide ligand comprising:
    a polypeptide of the amino acid sequence:
      (B-Ala)-Sar10-AC(D-Ala)NE(1Nal)(D-Ala)
      CEDFYD(tBuGly)C (SEQ ID NO: 5); and
    a molecular scaffold which is TBMB (1,3,5-tris (bromomethyl)benzene), which forms covalent bonds with the cysteine residues of the polypeptide yielding a tri-substituted 1,3,5-trismethylbenzene structure;
  $R_3$ represents methyl, and $R_1$, $R_2$ and $R_4$ each represent hydrogen;
  m represents 2; and
  n represents 1,
or a pharmaceutically acceptable salt thereof.

12. A pharmaceutical composition comprising the drug conjugate according to claim 11, in combination with one or more pharmaceutically acceptable excipients.

\* \* \* \* \*

SEQUENCE LISTING

<160> NUMBER OF SEQ ID NOS: 78

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic peptide -continued

```
<220> FEATURE:
<221> NAME/KEY: MOD_RES
<222> LOCATION: (2)..(2)
<223> OTHER INFORMATION: Xaa can be any naturally occurring amino acid
<220> FEATURE:
<221> NAME/KEY: MOD_RES
<222> LOCATION: (3)..(3)
<223> OTHER INFORMATION: Xaa represents either a polar, uncharged amino
      acid residue selected from N, C, Q, M, S and T or a non-polar
      aliphatic amino acid residue selected from G, A, I, L, P and V
<220> FEATURE:
<221> NAME/KEY: MOD_RES
<222> LOCATION: (4)..(5)
<223> OTHER INFORMATION: Xaa can be any naturally occurring amino acid
<220> FEATURE:
<221> NAME/KEY: MOD_RES
<222> LOCATION: (12)..(13)
<223> OTHER INFORMATION: Xaa can be any naturally occurring amino acid

<400> SEQUENCE: 1

Cys Xaa Xaa Xaa Xaa Gly Cys Glu Asp Phe Tyr Xaa Xaa Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Tyr Asn Glu Phe Gly Cys Glu Asp Phe Tyr Asp Ile Cys
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is beta Ala
<220> FEATURE:
<221> NAME/KEY: MOD_RES
<222> LOCATION: (2)..(2)
<223> OTHER INFORMATION: Xaa is Sar10

<400> SEQUENCE: 3

Xaa Xaa Ala Cys Tyr Asn Glu Phe Gly Cys Glu Asp Phe Tyr Asp Ile
1               5                   10                  15

Cys

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is D-Ala

<400> SEQUENCE: 4

Cys Xaa Asn Glu Phe Gly Cys Glu Asp Phe Tyr Asp Ile Cys
1               5                   10
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Beta Ala
<220> FEATURE:
<221> NAME/KEY: MOD_RES
<222> LOCATION: (2)..(2)
<223> OTHER INFORMATION: Xaa is Sar10
<220> FEATURE:
<221> NAME/KEY: MOD_RES
<222> LOCATION: (5)..(5)
<223> OTHER INFORMATION: Xaa is D-Ala
<220> FEATURE:
<221> NAME/KEY: MOD_RES
<222> LOCATION: (8)..(8)
<223> OTHER INFORMATION: Xaa is NAl
<220> FEATURE:
<221> NAME/KEY: MOD_RES
<222> LOCATION: (9)..(9)
<223> OTHER INFORMATION: Xaa is D-Ala
<220> FEATURE:
<221> NAME/KEY: MOD_RES
<222> LOCATION: (16)..(16)
<223> OTHER INFORMATION: Xaa is tBuGly

<400> SEQUENCE: 5

Xaa Xaa Ala Cys Xaa Asn Glu Xaa Xaa Cys Glu Asp Phe Tyr Asp Xaa
1               5                   10                  15

Cys

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is Y, M, F or V
<220> FEATURE:
<221> NAME/KEY: MOD_RES
<222> LOCATION: (3)..(3)
<223> OTHER INFORMATION: Xaa represents a polar, uncharged amino acid
      residue selected from N, C, Q, M, S and T or a non-polar aliphatic
      amino acid residue selected from G, A, I, L, P and V
<220> FEATURE:
<221> NAME/KEY: MOD_RES
<222> LOCATION: (4)..(4)
<223> OTHER INFORMATION: Xaa represents a polar, uncharged amino acid
      residue selected from N, C, Q, M, S and T or a polar, negatively
      charged amino acid residue selected from D or E
<220> FEATURE:
<221> NAME/KEY: MOD_RES
<222> LOCATION: (5)..(5)
<223> OTHER INFORMATION: Xaa represents a non-polar aromatic amino acid
      residue selected from F, W and Y
<220> FEATURE:
<221> NAME/KEY: MOD_RES
<222> LOCATION: (12)..(12)
<223> OTHER INFORMATION: Xaa represents a polar, negatively charged
      amino acid residue selected from D or E
<220> FEATURE:
<221> NAME/KEY: MOD_RES
<222> LOCATION: (13)..(13)
<223> OTHER INFORMATION: Xaa represents a non-polar aliphatic amino
```

-continued acid residue selected from G, A, I, L, P and V

<400> SEQUENCE: 6

Cys Xaa Xaa Xaa Xaa Gly Cys Glu Asp Phe Tyr Xaa Xaa Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is Y, M, F or V
<220> FEATURE:
<221> NAME/KEY: MOD_RES
<222> LOCATION: (3)..(3)
<223> OTHER INFORMATION: Xaa is N or G
<220> FEATURE:
<221> NAME/KEY: MOD_RES
<222> LOCATION: (4)..(4)
<223> OTHER INFORMATION: Xaa is E or Q

<400> SEQUENCE: 7

Cys Xaa Xaa Xaa Phe Gly Cys Glu Asp Phe Tyr Asp Ile Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is Y, M or F
<220> FEATURE:
<221> NAME/KEY: MOD_RES
<222> LOCATION: (3)..(3)
<223> OTHER INFORMATION: Xaa is N or G
<220> FEATURE:
<221> NAME/KEY: MOD_RES
<222> LOCATION: (4)..(4)
<223> OTHER INFORMATION: Xaa is E or Q

<400> SEQUENCE: 8

Cys Xaa Xaa Xaa Phe Gly Cys Glu Asp Phe Tyr Asp Ile Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is Y or M
<220> FEATURE:
<221> NAME/KEY: MOD_RES
<222> LOCATION: (4)..(4)
<223> OTHER INFORMATION: Xaa is E or Q

<400> SEQUENCE: 9

Cys Xaa Asn Xaa Phe Gly Cys Glu Asp Phe Tyr Asp Ile Cys

```
<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Met Asn Gln Phe Gly Cys Glu Asp Phe Tyr Asp Ile Cys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Phe Gly Glu Phe Gly Cys Glu Asp Phe Tyr Asp Ile Cys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Val Asn Glu Phe Gly Cys Glu Asp Phe Tyr Asp Ile Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Phe Asn Glu Phe Gly Cys Glu Asp Phe Tyr Asp Ile Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Tyr Asn Glu Tyr Gly Cys Glu Asp Phe Tyr Asp Ile Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 15

Cys Tyr Asn Glu Trp Gly Cys Glu Asp Phe Tyr Asp Ile Cys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Lys Asn Arg Gly Phe Gly Cys Glu Asp Phe Tyr Asp Ile Cys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Glu Asp Phe Tyr Asp Ile Cys
1               5

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Cys Tyr Asn Glu Phe Gly Cys Glu Asp Phe Tyr Asp Ile Cys Ala
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Cys Met Asn Gln Phe Gly Cys Glu Asp Phe Tyr Asp Ile Cys Ala
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is Sar10

<400> SEQUENCE: 20

Gly Xaa Ala Cys Tyr Asn Glu Phe Gly Cys Glu Asp Phe Tyr Asp Ile

Cys
1               5              10             15

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Asn Glu Phe
1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Asn Glu Phe Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Asp Phe Tyr Asp Ile
1               5

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Cys Asn Arg Trp Gly Cys Glu Asp Phe Tyr Asp Ile Cys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Y, W, H, A, M, R, S, G, D, Q, E, L, or T
<220> FEATURE:
<221> NAME/KEY: MOD_RES
<222> LOCATION: (4)..(4)
<223> OTHER INFORMATION: E, A, P, D, Q, I, R, Y, F, S, V, H, L, T, M, W,
      K or G
<220> FEATURE:
<221> NAME/KEY: MOD_RES

```
<222> LOCATION: (5)..(5)
<223> OTHER INFORMATION: W, Y or F

<400> SEQUENCE: 25

Cys Xaa Asn Xaa Xaa Gly Cys Glu Asp Phe Tyr Asp Ile Cys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Trp Asn Ala Trp Gly Cys Glu Asp Phe Tyr Asp Ile Cys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys His Asn Pro Tyr Gly Cys Glu Asp Phe Tyr Asp Ile Cys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ala Asn Asp Tyr Gly Cys Glu Asp Phe Tyr Asp Ile Cys
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Met Asn Glu Trp Gly Cys Glu Asp Phe Tyr Asp Ile Cys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Ala Asn Gln Trp Gly Cys Glu Asp Phe Tyr Asp Ile Cys
1               5                   10
```

```
<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Arg Asn Pro Trp Gly Cys Glu Asp Phe Tyr Asp Ile Cys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Ser Asn Ile Trp Gly Cys Glu Asp Phe Tyr Asp Ile Cys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Ser Asn Gln Trp Gly Cys Glu Asp Phe Tyr Asp Ile Cys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Gly Asn Glu Tyr Gly Cys Glu Asp Phe Tyr Asp Ile Cys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Gly Asn Arg Trp Gly Cys Glu Asp Phe Tyr Asp Ile Cys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Cys Gly Asn Tyr Trp Gly Cys Glu Asp Phe Tyr Asp Ile Cys
1               5                   10
```

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Cys Met Asn Glu Tyr Gly Cys Glu Asp Phe Tyr Asp Ile Cys
1               5                   10
```

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Cys Ser Asn Pro Trp Gly Cys Glu Asp Phe Tyr Asp Ile Cys
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Cys Asp Asn Ala Trp Gly Cys Glu Asp Phe Tyr Asp Ile Cys
1               5                   10
```

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Cys His Asn Ala Trp Gly Cys Glu Asp Phe Tyr Asp Ile Cys
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Cys Gln Asn Tyr Trp Gly Cys Glu Asp Phe Tyr Asp Ile Cys
1               5                   10
```

<210> SEQ ID NO 42
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 42

Cys Ser Asn Gln Tyr Gly Cys Glu Asp Phe Tyr Asp Ile Cys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Ala Asn Gln Tyr Gly Cys Glu Asp Phe Tyr Asp Ile Cys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Gly Asn Ala Tyr Gly Cys Glu Asp Phe Tyr Asp Ile Cys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Ser Asn Phe Trp Gly Cys Glu Asp Phe Tyr Asp Ile Cys
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys His Asn Gln Tyr Gly Cys Glu Asp Phe Tyr Asp Ile Cys
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Tyr Asn Ser Tyr Gly Cys Glu Asp Phe Tyr Asp Ile Cys
1               5                   10
```

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Glu Asn Ala Trp Gly Cys Glu Asp Phe Tyr Asp Ile Cys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Ala Asn Tyr Trp Gly Cys Glu Asp Phe Tyr Asp Ile Cys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Gly Asn Asp Trp Gly Cys Glu Asp Phe Tyr Asp Ile Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Ala Asn Arg Phe Gly Cys Glu Asp Phe Tyr Asp Ile Cys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Arg Asn Ala Trp Gly Cys Glu Asp Phe Tyr Asp Ile Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 53

Cys Gly Asn Val Phe Gly Cys Glu Asp Phe Tyr Asp Ile Cys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Ser Asn His Trp Gly Cys Glu Asp Phe Tyr Asp Ile Cys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Glu Asn Glu Tyr Gly Cys Glu Asp Phe Tyr Asp Ile Cys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Ala Asn Phe Trp Gly Cys Glu Asp Phe Tyr Asp Ile Cys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Gly Asn Leu Trp Gly Cys Glu Asp Phe Tyr Asp Ile Cys
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Leu Asn Gln Tyr Gly Cys Glu Asp Phe Tyr Asp Ile Cys
1               5                   10

<210> SEQ ID NO 59
<211> LENGTH: 14
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 59

Cys Tyr Asn His Phe Gly Cys Glu Asp Phe Tyr Asp Ile Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Tyr Asn Thr Phe Gly Cys Glu Asp Phe Tyr Asp Ile Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Ala Asn Asp Phe Gly Cys Glu Asp Phe Tyr Asp Ile Cys
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Ser Asn Met Trp Gly Cys Glu Asp Phe Tyr Asp Ile Cys
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Arg Asn Trp Trp Gly Cys Glu Asp Phe Tyr Asp Ile Cys
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Ser Asn Leu Trp Gly Cys Glu Asp Phe Tyr Asp Ile Cys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Arg Asn Asp Trp Gly Cys Glu Asp Phe Tyr Asp Ile Cys
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Leu Asn Arg Trp Gly Cys Glu Asp Phe Tyr Asp Ile Cys
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Met Asn Asp Trp Gly Cys Glu Asp Phe Tyr Asp Ile Cys
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Arg Asn Ser Tyr Gly Cys Glu Asp Phe Tyr Asp Ile Cys
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Ser Asn Glu Phe Gly Cys Glu Asp Phe Tyr Asp Ile Cys
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 70

Cys Gly Asn Pro Trp Gly Cys Glu Asp Phe Tyr Asp Ile Cys
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Arg Asn Lys Trp Gly Cys Glu Asp Phe Tyr Asp Ile Cys
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Gly Asn Leu Phe Gly Cys Glu Asp Phe Tyr Asp Ile Cys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Gln Asn Arg Tyr Gly Cys Glu Asp Phe Tyr Asp Ile Cys
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Arg Asn Leu Trp Gly Cys Glu Asp Phe Tyr Asp Ile Cys
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Gly Asn Leu Tyr Gly Cys Glu Asp Phe Tyr Asp Ile Cys
1               5                   10

<210> SEQ ID NO 76
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Gly Asn Gly Tyr Gly Cys Glu Asp Phe Tyr Asp Ile Cys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Thr Asn Arg Trp Gly Cys Glu Asp Phe Tyr Asp Ile Cys
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Tyr Asn Leu Trp Gly Cys Glu Asp Phe Tyr Asp Ile Cys
1               5                   10
```